United States Patent
Lauber et al.

(10) Patent No.: US 12,252,557 B2
(45) Date of Patent: Mar. 18, 2025

(54) CHARGED SURFACE REVERSED PHASE CHROMATOGRAPHIC MATERIALS METHOD FOR ANALYSIS OF GLYCANS MODIFIED WITH AMPHIPATHIC, STRONGLY BASIC MOIETIES

(71) Applicant: Waters Technologies Corporation, Milford, MA (US)

(72) Inventors: Matthew A. Lauber, North Smithfield, RI (US); Scott A. McCall, Smithfield, RI (US); Babajide Okandeji, Providence, RI (US); Pamela C. Iraneta, Brighton, MA (US)

(73) Assignee: Waters Technologies Corporation, Milford, MA (US)

( * ) Notice: Subject to any disclaimer, the term of this patent is extended or adjusted under 35 U.S.C. 154(b) by 337 days.

(21) Appl. No.: 16/095,919

(22) PCT Filed: Apr. 21, 2017

(86) PCT No.: PCT/US2017/028856
§ 371 (c)(1),
(2) Date: Oct. 23, 2018

(87) PCT Pub. No.: WO2017/189357
PCT Pub. Date: Nov. 2, 2017

(65) Prior Publication Data
US 2020/0332028 A1 Oct. 22, 2020

Related U.S. Application Data

(60) Provisional application No. 62/326,783, filed on Apr. 24, 2016.

(51) Int. Cl.
| | | |
|---|---|---|
| *C07B 37/00* | (2006.01) | |
| *B01D 15/32* | (2006.01) | |
| *B01D 15/36* | (2006.01) | |
| *B01D 15/38* | (2006.01) | |
| *C08B 37/00* | (2006.01) | |
| *G01N 33/58* | (2006.01) | |

(52) U.S. Cl.
CPC .......... *C08B 37/006* (2013.01); *B01D 15/327* (2013.01); *B01D 15/363* (2013.01); *B01D 15/3847* (2013.01); *G01N 33/58* (2013.01)

(58) Field of Classification Search
CPC .......... G01N 33/58; G01N 2030/8836; B01D 15/36; B01D 15/363; B01D 15/3847; B01D 15/327; C07H 13/12; C07H 1/06; C08B 37/006
See application file for complete search history.

(56) References Cited

U.S. PATENT DOCUMENTS

| | | |
|---|---|---|
| 2013/0319086 A1 | 12/2013 | Wyndham et al. |
| 2014/0178912 A1 | 6/2014 | Liu et al. |
| 2014/0242709 A1 | 8/2014 | Brousmiche et al. |
| 2015/0204824 A1 | 7/2015 | Lauber et al. |

FOREIGN PATENT DOCUMENTS

| | | |
|---|---|---|
| JP | S61278759 A | 12/1986 |
| JP | 2007522476 A | 8/2007 |
| JP | 2013501243 A | 1/2013 |
| JP | 2013505028 A | 2/2013 |
| JP | 2014534176 A | 12/2014 |
| WO | 2011017418 A1 | 2/2011 |
| WO | 2011035884 A1 | 3/2011 |
| WO | 2013049622 A1 | 4/2013 |
| WO | 2015/166399 A1 | 11/2015 |
| WO | 2018067398 A1 | 4/2018 |

OTHER PUBLICATIONS

Wiczling et al. pH/Organic Solvent Double-Gradient Reversed-Phase HPLC. Anal. Chem. 2005, vol. 77, pp. 449-458. (Year: 2005).*

Suzuki et al. Dual-gradient high-performance liquid chromatography for identification of cytosolic high-mannose-type free glycans. Analytical Biochemistry 2008, vol. 381, pp. 224-232. (Year: 2008).*

International Search Report and Written Opinion for International Application No. PCT/US2017/028856 mailed Nov. 20, 2017, 15 pages.

Lauber, M. A., et al., "Rapid Preparation of Released N-Glycans for HILIC Analysis Using a Labeling Reagent that Facilitates Sensitive Fluorescence and ESI-MS Detection", Analytical Chemistry, 87(10): 5401-5409 (2015).

Extended European Search Report for Application No. EP17790151.9, mailed Nov. 26, 2019, 10 pages.

Yan, S., et al., "Comparision of RP-HPLC modes to analyse the N-glycome of the free-living nematode Pristionchus pacificus: Liquid Phase Separations", Electrophoresis, 36(11-12):1314-1329 (2015).

Kallberg, K., et al., "Application of a pH responsive multimodal hydrophobic interaction chromatography medium for the analysis of glycosylated proteins", Journal of Chromatography A, 1218(5):678-683 (2011).

Knezevic, A., et al., "High throughout plasma N-glycome profiling using multiplexed labelling and UPLC with fluorescence detection", Analyst 136(22):4670-4673 (2011).

(Continued)

Primary Examiner — Shafiqul Haq
(74) Attorney, Agent, or Firm — WOMBLE BOND DICKINSON (US) LLP; Deborah M. Vernon; Ricardo Joseph

(57) ABSTRACT

The present invention provides novel methods for the chromatographic analysis of glycans using high purity chromatographic materials comprising a chromatographic surface wherein the chromatographic surface comprises a hydrophobic surface group and one or more ionizable modifier and a labeling reagent which is capable of providing amphipathic and strongly basic labeling moieties to a sample to be analyzed.

22 Claims, 16 Drawing Sheets

(56) References Cited

OTHER PUBLICATIONS

International Preliminary Report on Patentability for International application No. PCT/US2017/028856, issued on Oct. 30, 2018, 13 pages.
International Search Report and Written Opinion for International application No. PCT/US2017/028856, mailed on Nov. 20, 2017, 15 pages.
International Preliminary Report on Patentability for International Application No. PCT/US2017/028856 mailed Nov. 8, 2018, 8 pages.

* cited by examiner

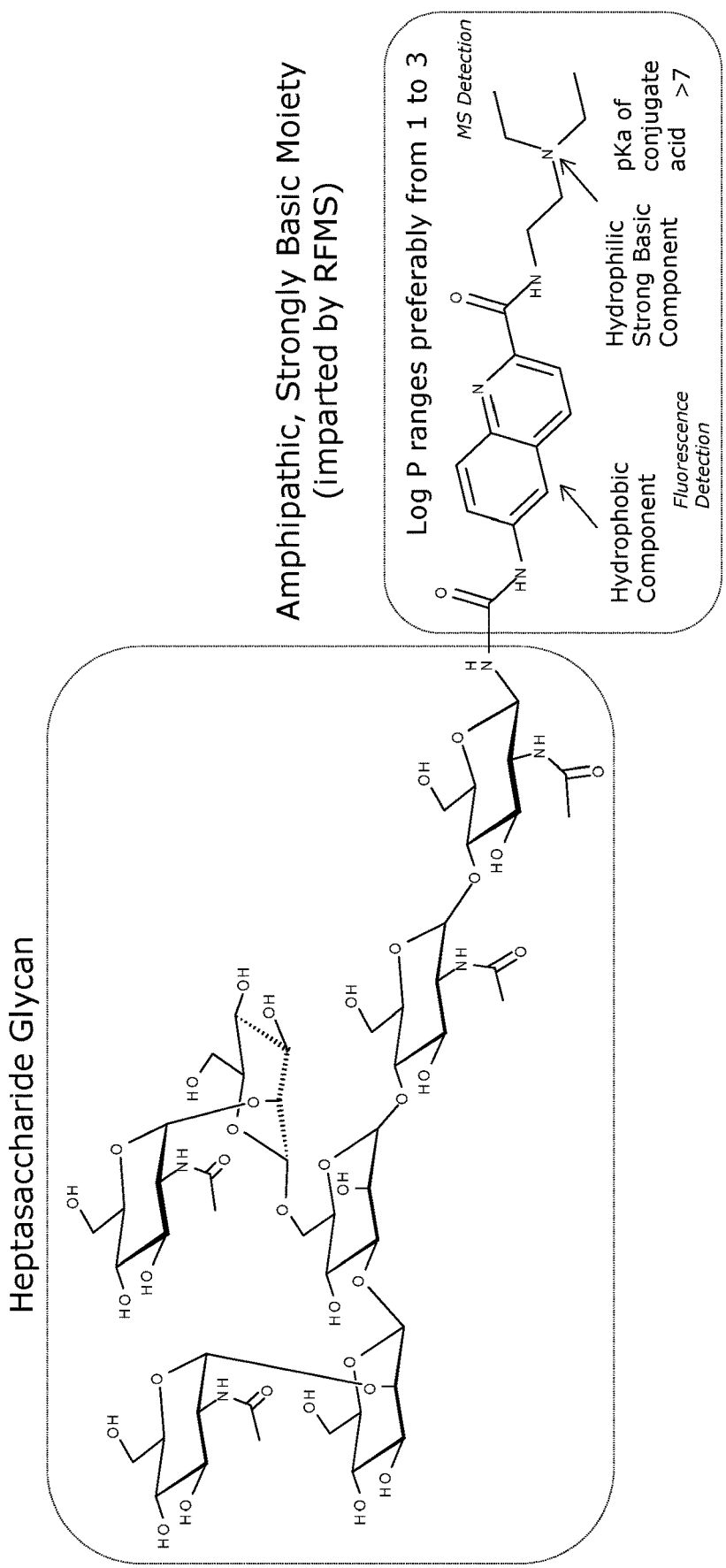
FIG. 1. Example chemical structure of a glycan modified with a amphipathic, strongly basic moiety. A heptasaccharide glycan labeled with RFMS.

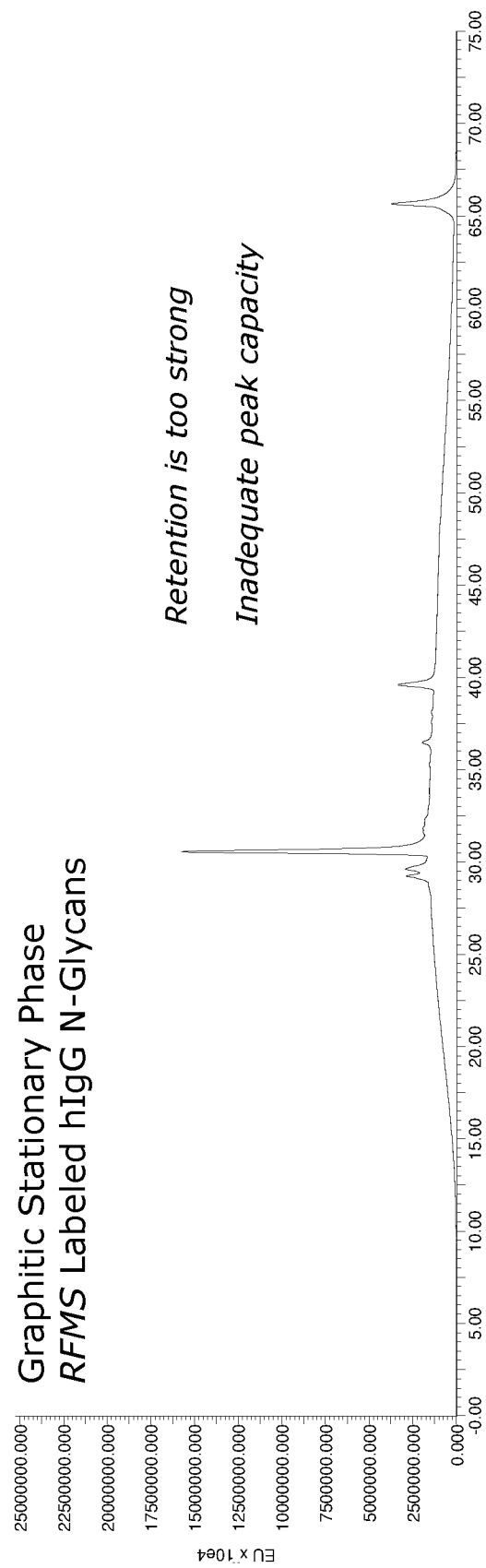
FIG. 2. Fluorescence chromatogram resulting from the use of a Thermo Hypercarb 250Å 3μm 2.1 × 150 mm column showing that RFMS labeled N-glycans are too strongly retained and inadequately resolved using a graphitic stationary phase. Separation conditions can be found in Example 2.

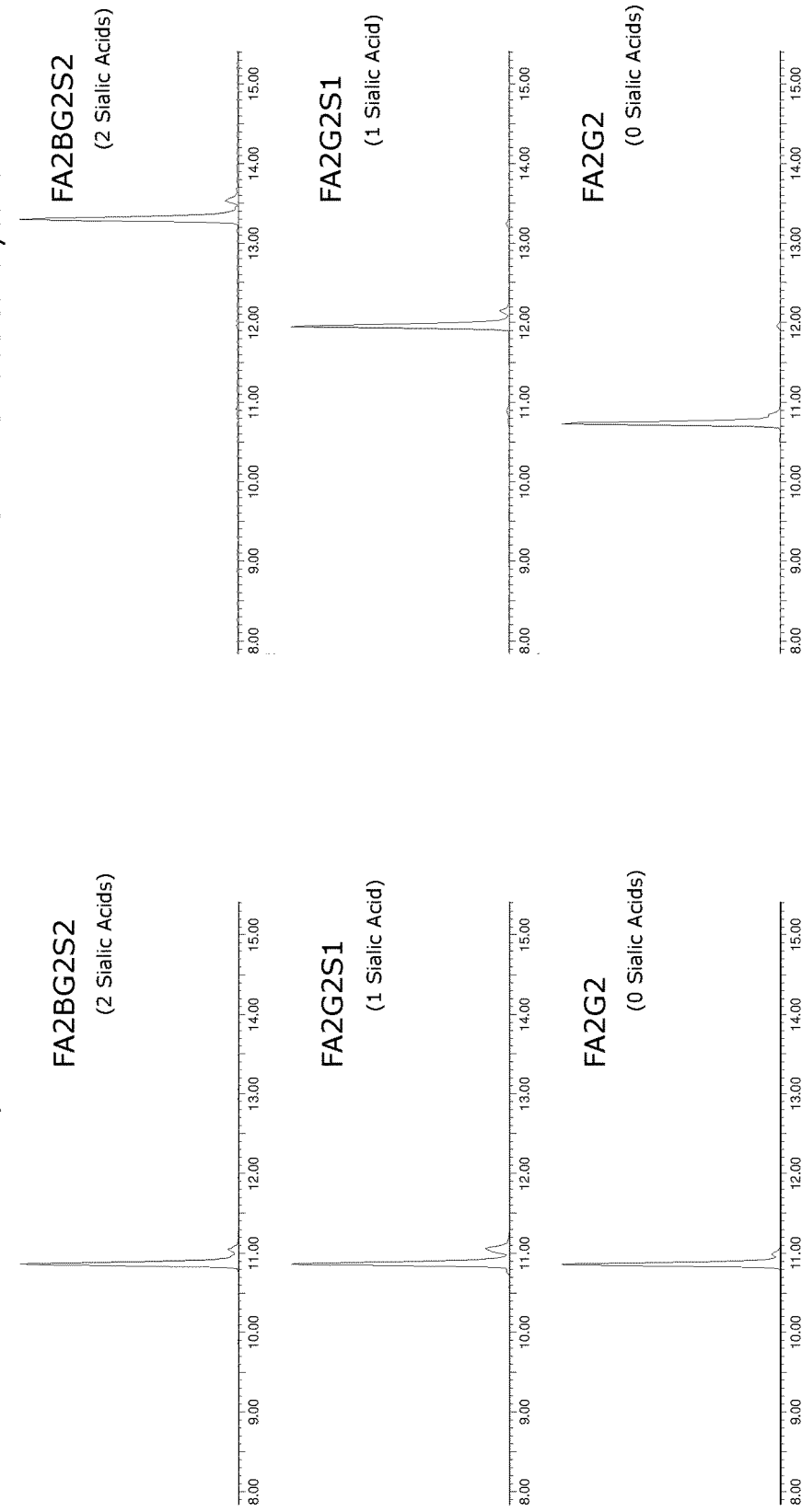
FIG. 3. Conventional C18 separations of RFMS labeled glycans provide insufficient selectivity. Extracted ion chromatograms for FA2G2, FA2G2S1, and FA2BG2S2 resulting from the use of a conventional C18 reversed phase material. (B) An example of desirable selectivity that could be achieved with an HPCM. Separation conditions are described in Example 2.

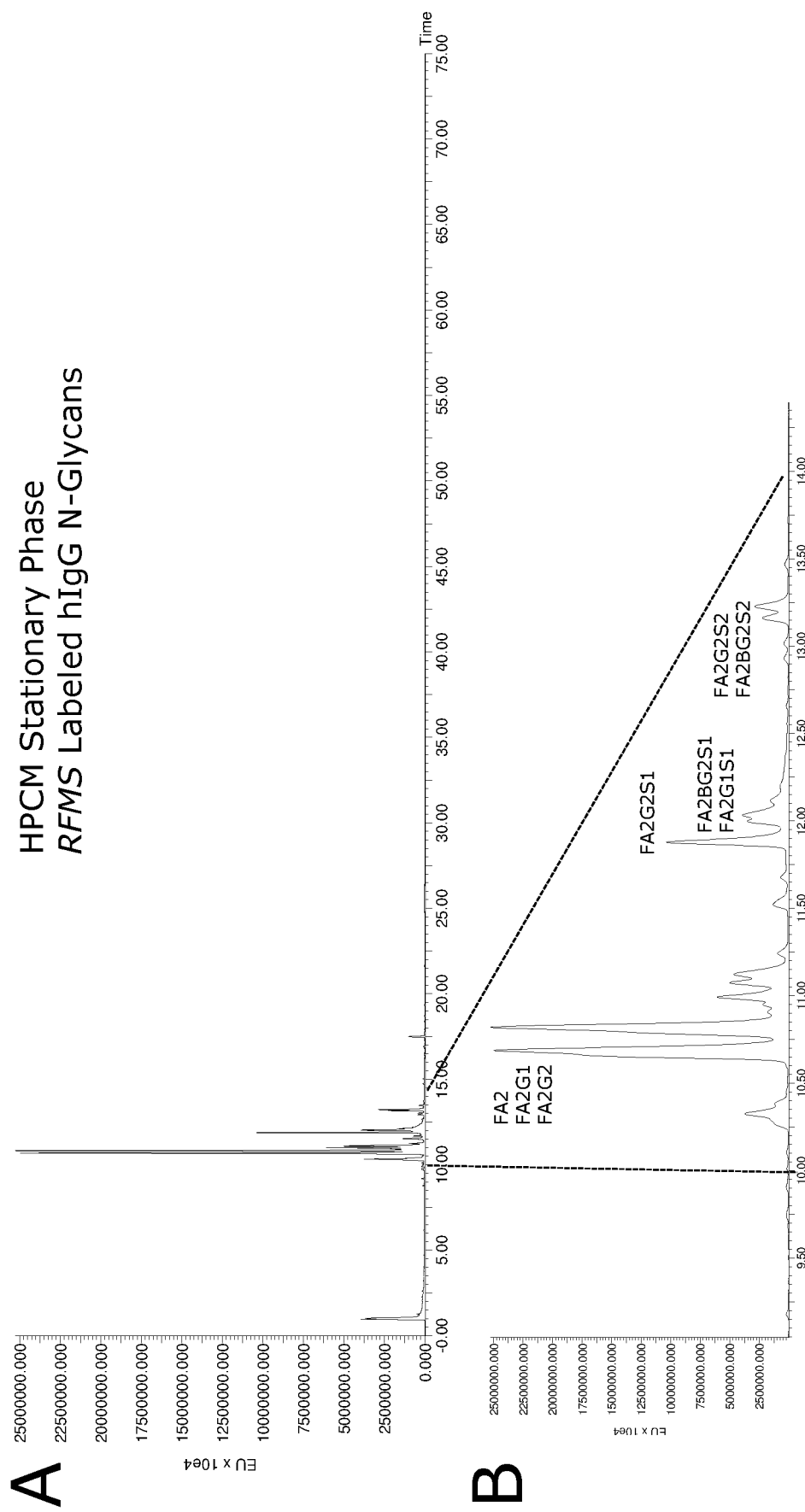

FIG. 4. Fluorescence chromatogram resulting from the use of a Waters ACQUITY UPLC HPCM 130Å 1.7μm 2.1 x 150 mm column showing that RFMS labeled N-glycans are retained and uniquely separated with high peak capacity using an HPCM. (A) Full view (B) Zoomed view of the observed chromatographic peaks and their MS based assignments to neutral, monosialylated and disialylated glycans structures. Separation conditions are described in Example 3.

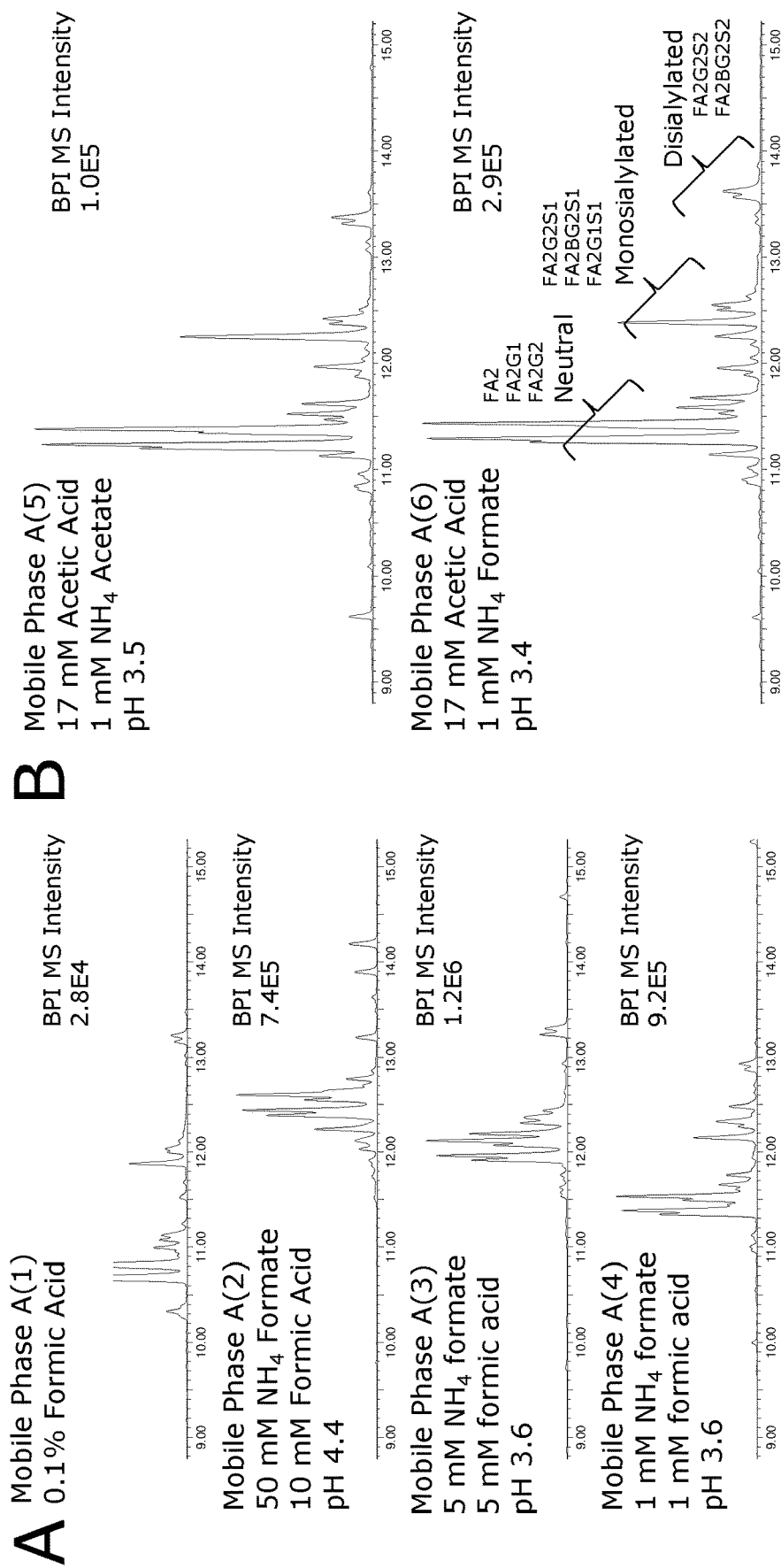

FIG. 5. MS sensitivity, retentivity and selectivity of RFMS hIgG glycan separations are modulated through the use of various aqueous mobile phase additives. (A) Fluorescence chromatograms of RFMS labeled hIgG glycans separated with a Waters ACQUITY UPLC HPCM 130Å 1.7μm 2.1 x 150 mm column and ammonium/formic acid based buffers. (B) Fluorescence chromatograms of RFMS labeled hIgG glycans separated with a Waters ACQUITY UPLC HPCM 130Å 1.7μm 2.1 x 150 mm and ammonium formate/acetic acid based buffers. Separation conditions are described in Example 4.

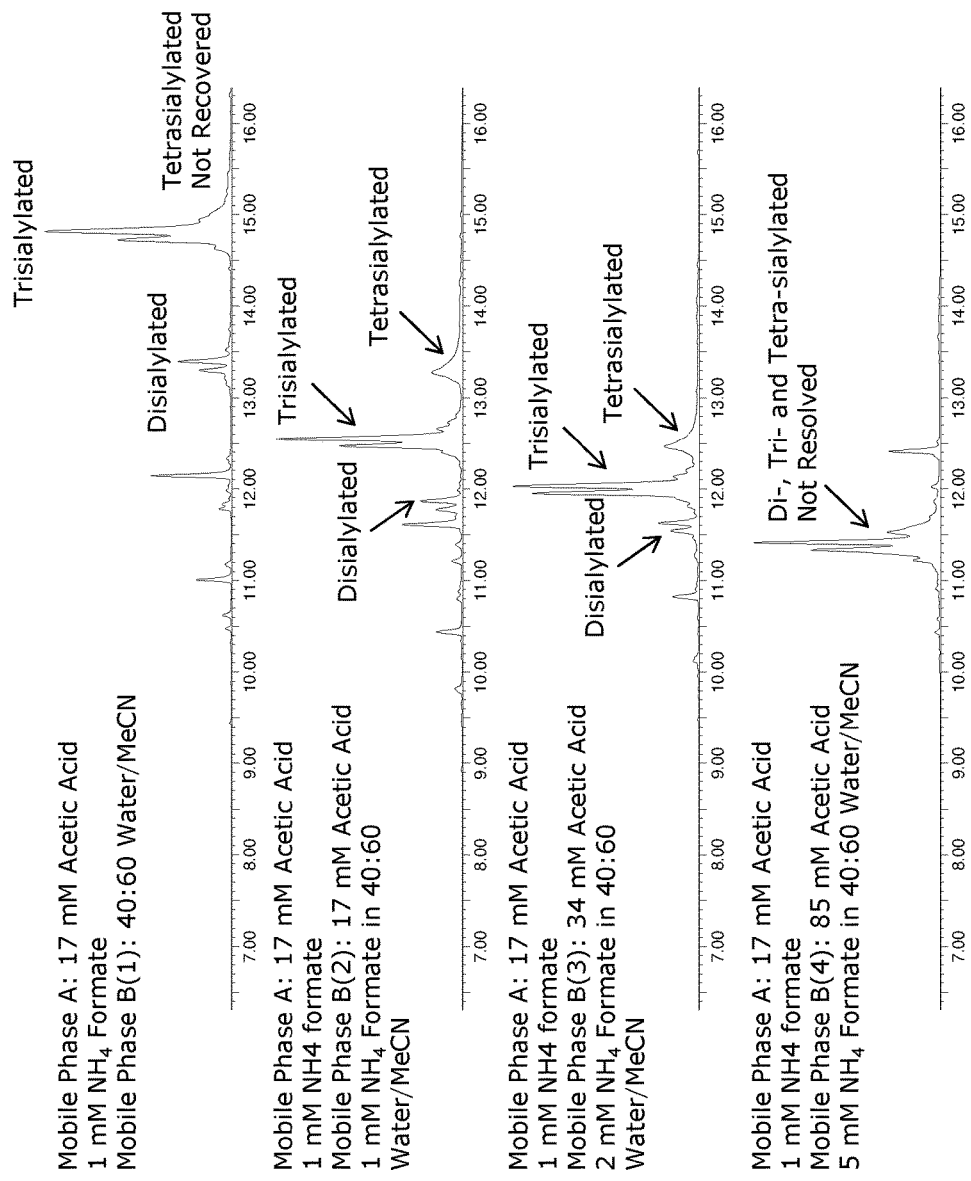

FIG. 6. Constant ionic strength separations are advantageous for resolving highly sialylated RFMS glycans with HPCM. (A) Fluorescence chromatograms of RFMS labeled fetuin glycans separated with a Waters ACQUITY UPLC HPCM 130Å 1.7μm 2.1 x 150 mm column and eluent mobile phases containing varying compositions of ammonium formate/acetic acid based buffers. 'MeCN' stands for acetonitrile. Separation conditions are described in Example 5.

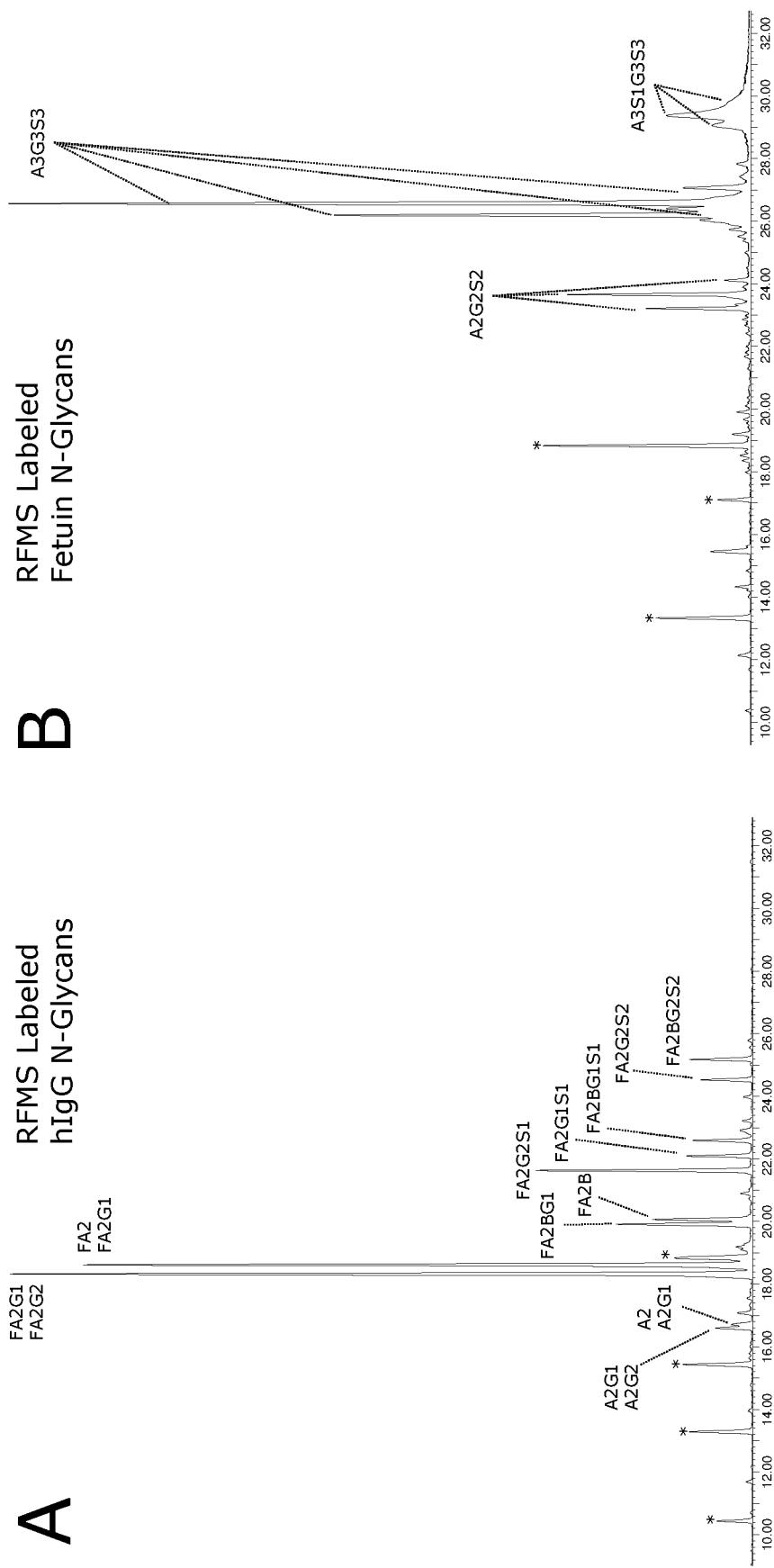
FIG. 7. Optimized separations of RFMS glycans using HPCM column chromatography. Fluorescence chromatograms of (A) RFMS labeled hIgG glycans and (B) RFMS labeled fetuin glycans as obtained with a Waters ACQUITY UPLC HPCM 130Å 1.7μm 2.1 x 150 mm column. MS based identifications are provided. Separation conditions are described in Example 6.

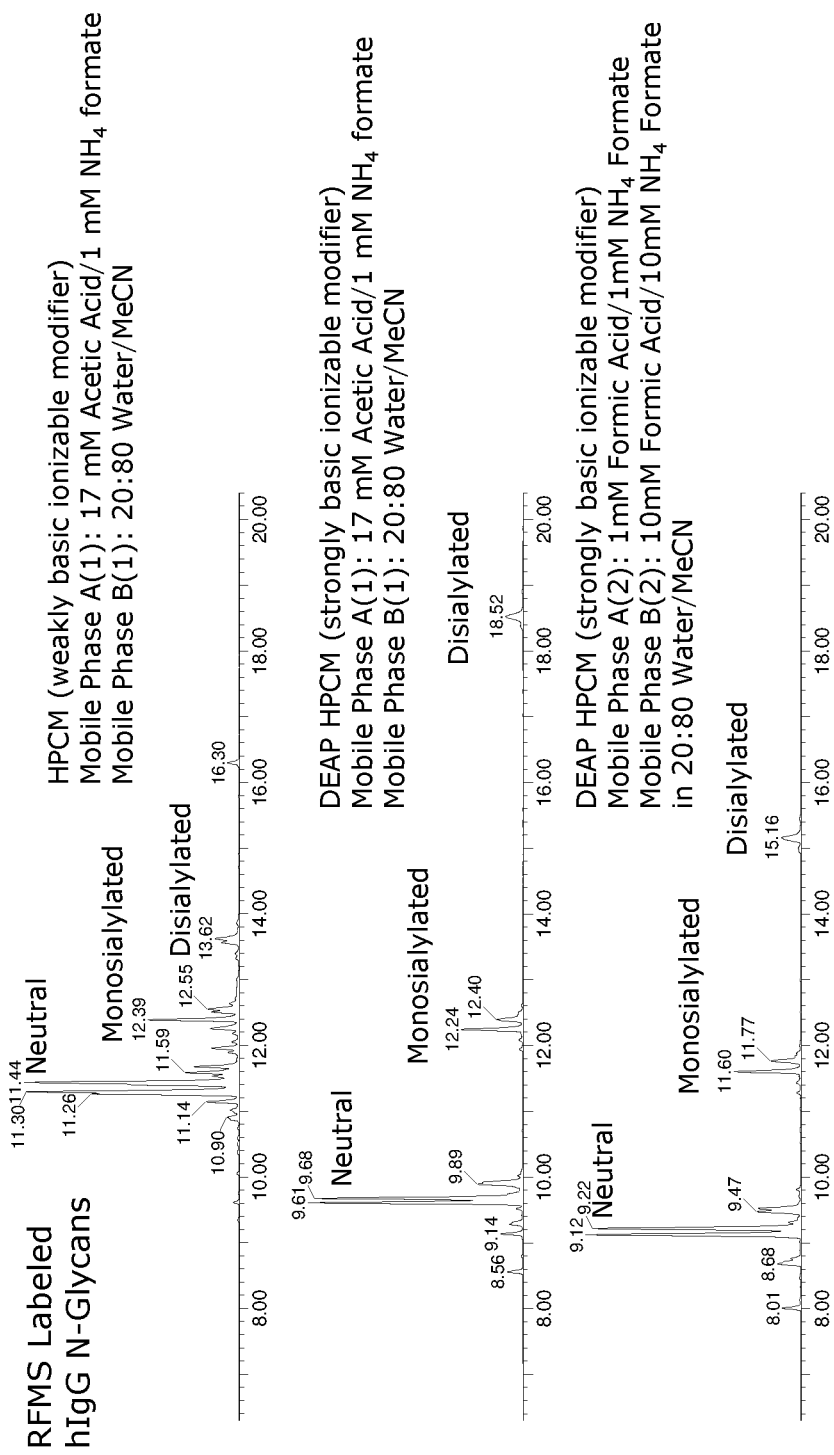
FIG. 8. An HPCM with a strongly basic, versus weakly basic, ionizable modifier requires different mobile phase optimization. Fluorescence chromatograms of RFMS labeled hIgG glycans as obtained with a DEAP HPCM 130Å 1.7μm 2.1 x 150 mm column. Mobile phases A and B and defined for each separation. 'MeCN' denotes acetonitrile. Separation conditions are described in Example 7.

FIG.9. An HPCM with a strongly basic, versus weakly basic, ionizable modifier requires different mobile phase optimization. Fluorescence chromatograms of RFMS labeled hIgG glycans as obtained with a DEAP HPCM 130Å 1.7µm 2.1 x 150 mm column. Gradient conditions are defined for each separation. Separation conditions are described in Example 8.

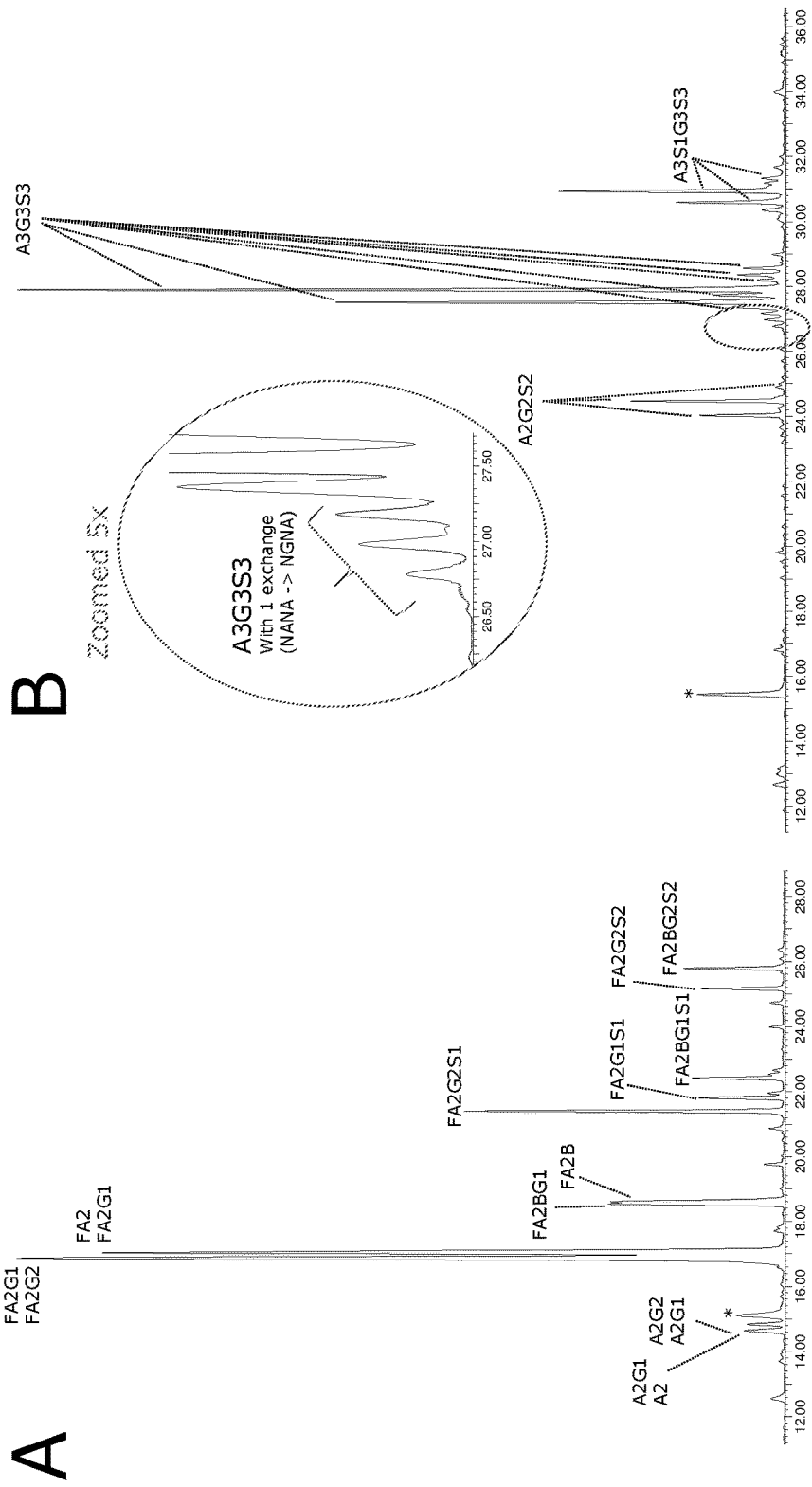
FIG. 10. Optimized separations of RFMS glycans using the DEAP HPCM column chromatography. Fluorescence chromatograms of (A) RFMS labeled hIgG glycans and (B) RFMS labeled fetuin glycans as obtained with a DEAP HPCM 130Å 1.7μm 2.1 x 150 mm column. MS based identifications are provided. Asterisks mark non-glycan peaks. Separation conditions are described in Example 9.

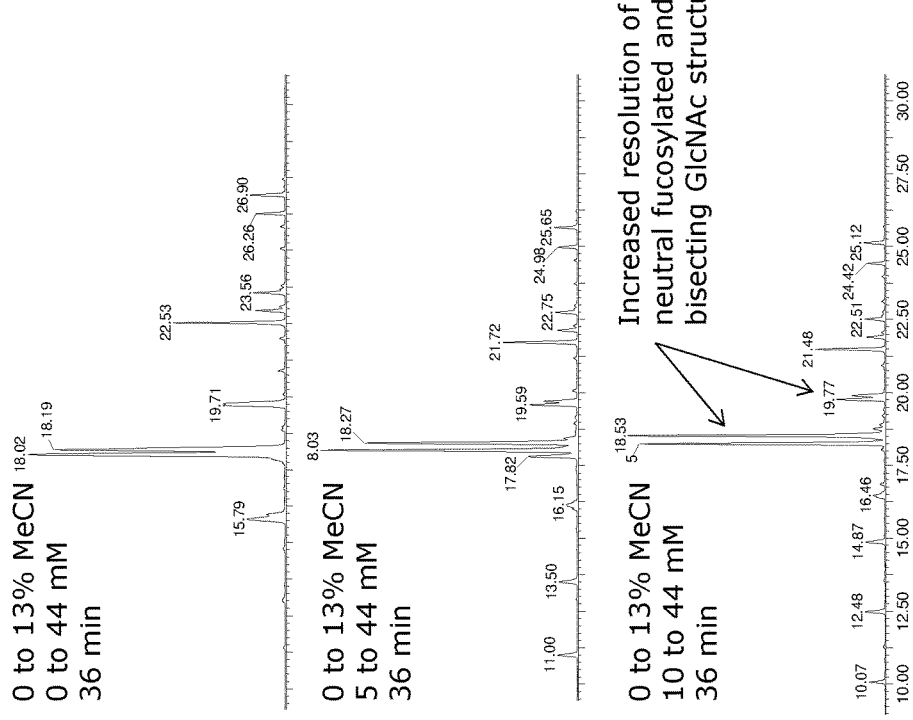

FIG. 11. Separations of RFMS glycans using the DEAP HPCM (Phase 1A) column chromatography can be improved by adjusting initial conditions to have an ionic strength between 0 and 10 mM ammonium formate/formic acid buffer. Fluorescence chromatograms of RFMS labeled hIgG glycans obtained with a DEAP HPCM 130Å 1.7μm 2.1 x 150 mm column and different ionic strengths for initial conditions: 0, 5 and 10 mM ammonium formate/formic acid buffer. Gradient conditions are provided. 'MeCN' denotes acetonitrile. Separation conditions are described in Example 10.

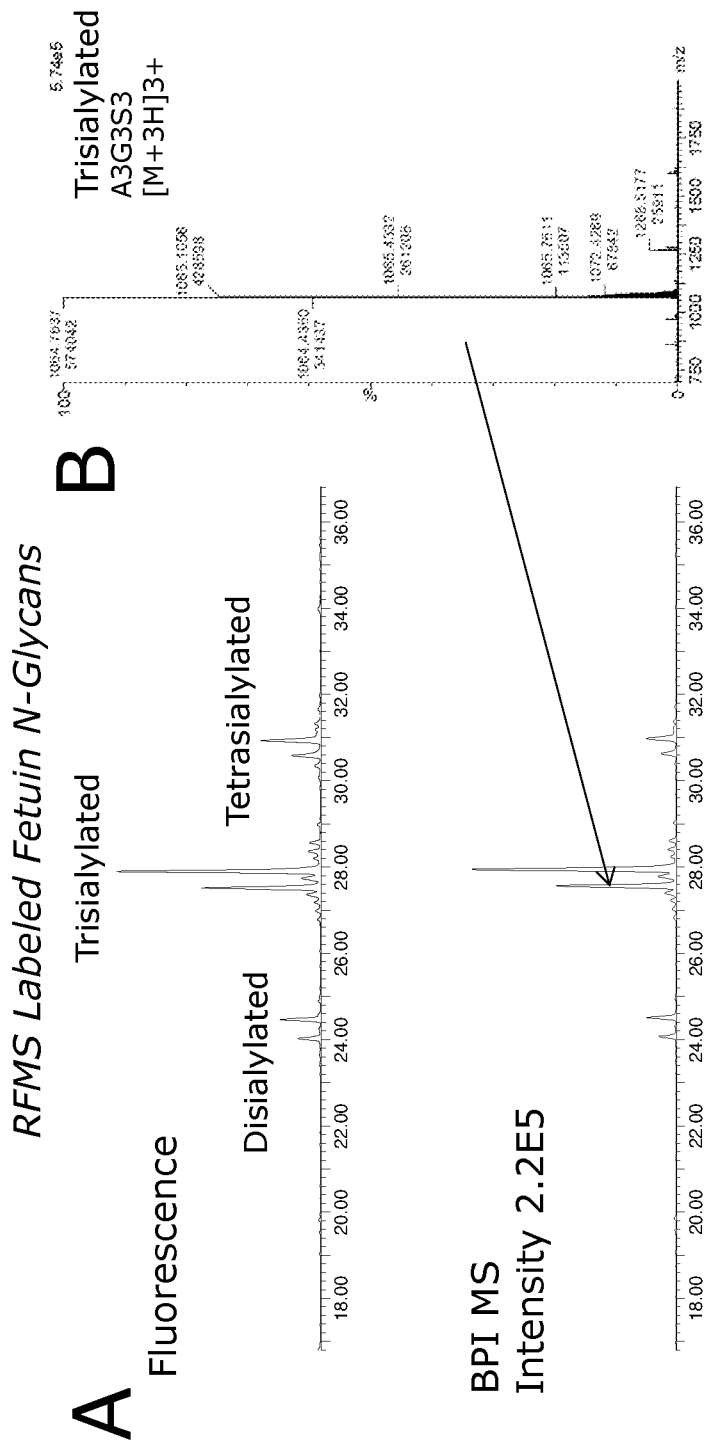

FIG. 12. Separation conditions optimal for the DEAP HPCM (Phase 1A) HPCM support high sensitivity ESI+MS detection. (A) Fluorescence and base peak intensity (BPI) chromatograms of RFMS labeled bovine fetuin glycans obtained with a DEAP HPCM 130Å 1.7μm 2.1 x 150 mm column and optimal method conditions. (B) A high signal-to-noise, low background ESI+ mass spectrum corresponding to the A3G3S3 RFMS glycan eluting at the marked retention time. Separation conditions are described in Example 9.

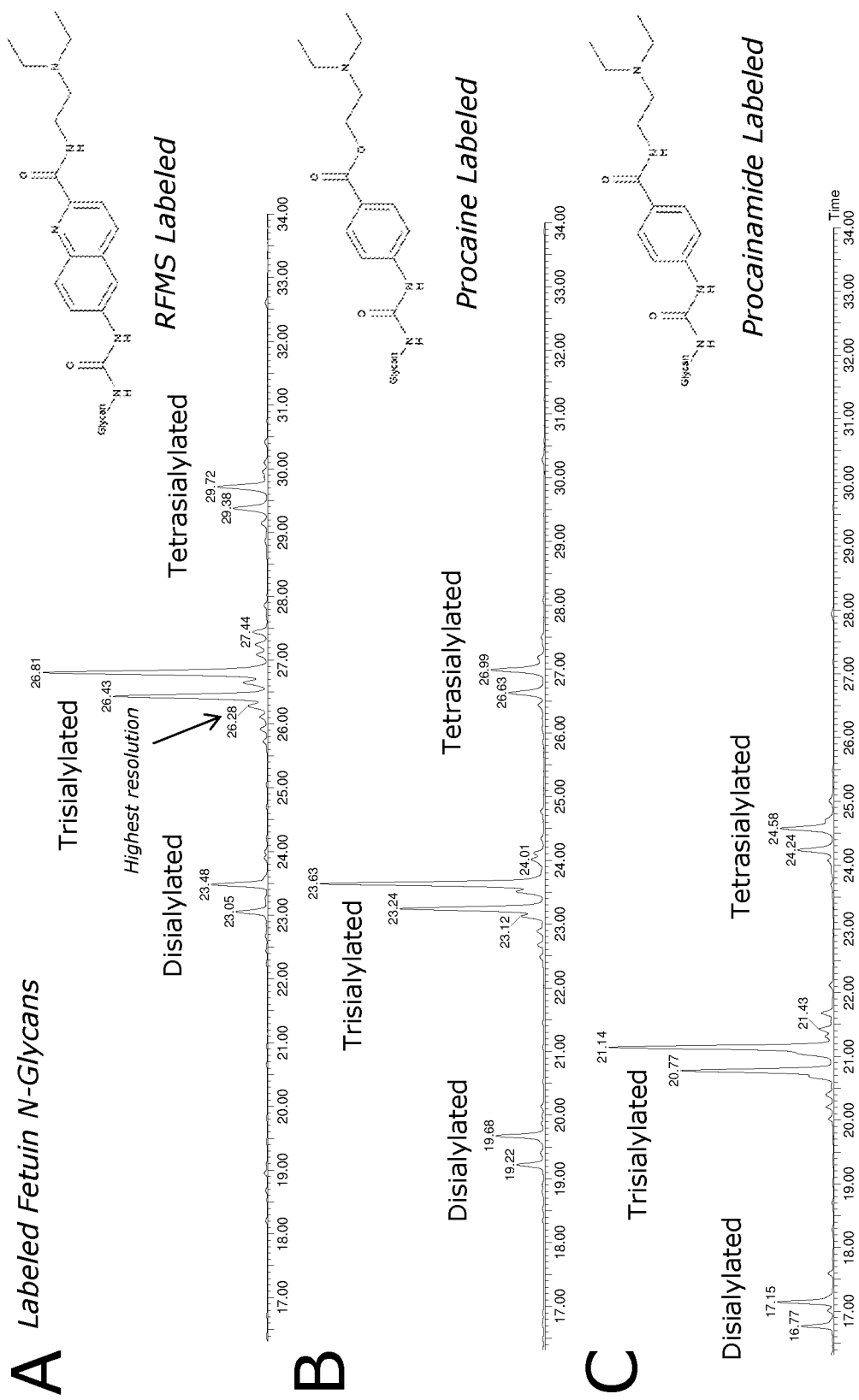
FIG. 13. Optimized separations of released fetuin glycans labeled with various amphipathic, strongly basic moieties. Fluorescence chromatograms of (A) RFMS labeled, (B) procaine labeled, and (C) procainamide labeled fetuin N-glycans as obtained with a DEAP HPCM 130Å 1.7μm (Phase 1A) 2.1 x 150 mm column. Separation conditions are described in Example 11.

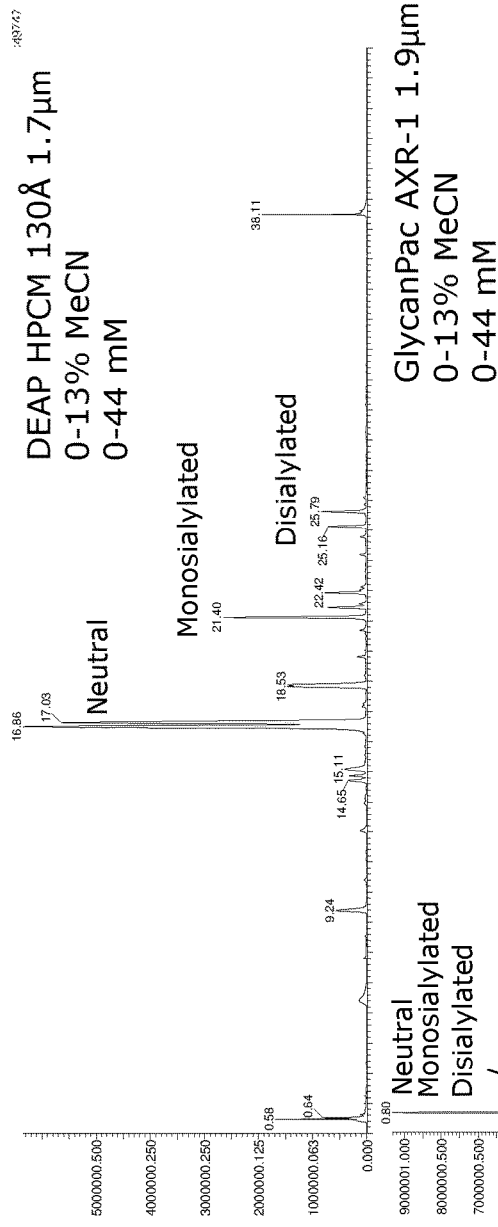
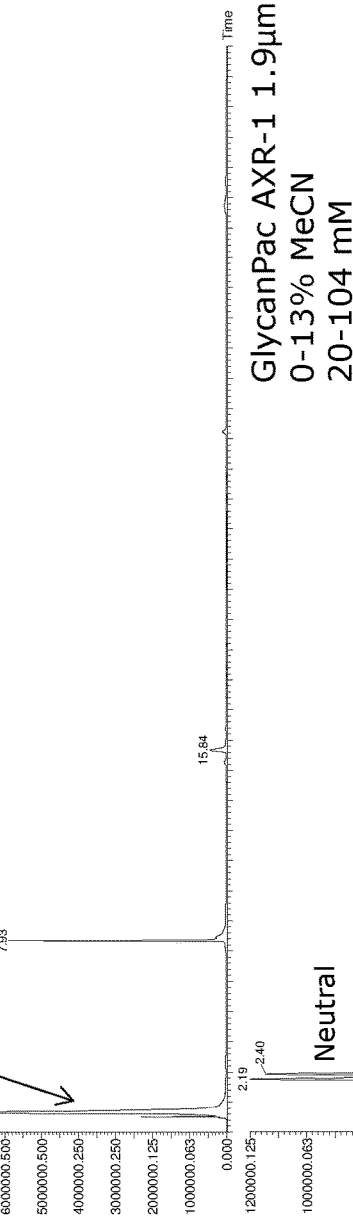

FIG. 14. Comparison example. Separations of RFMS glycans using the DEAP HPCM material (DEAP HPCM, Phase 1A) versus a commercially available mixed mode GlycanPac AXR-1 column. Fluorescence chromatograms of RFMS labeled hIgG glycans obtained with a DEAP HPCM 130Å 1.7μm 2.1 x 150 mm column under optimal conditions versus a GlycanPac AXR-1 2.1x150 mm column under identical and optimized conditions. Gradient changes are noted for each separations, include change in acetonitrile (MeCN) and change in buffer strength of ammonium formate/formic acid. Separation conditions are described in Example 12.

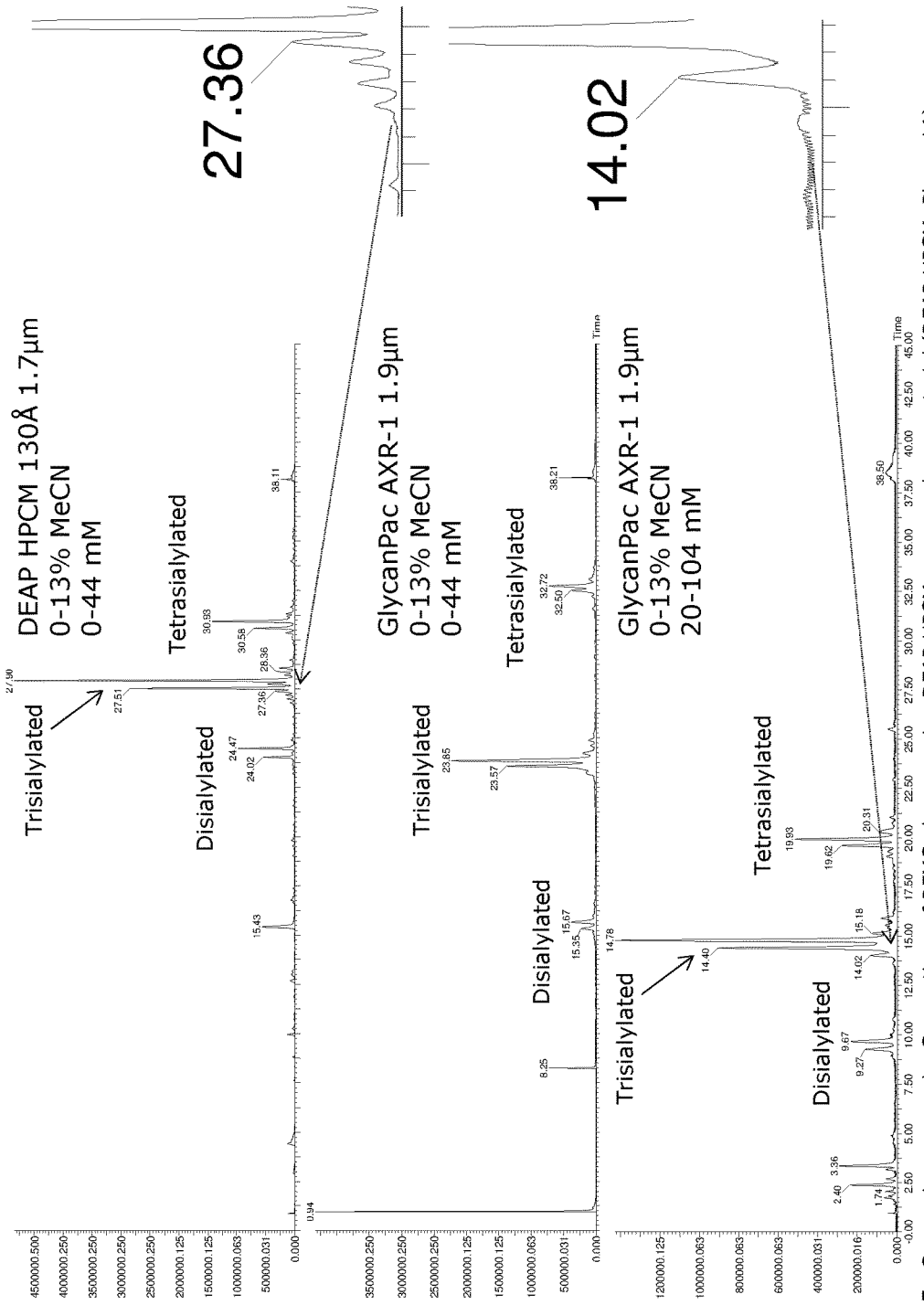

FIG 15. Comparison example. Separations of RFMS glycans using DEAP HPCM reverse phase material (DEAP HPCM, Phase 1A) versus a commercially available mixed mode GlycanPac AXR-1 column. Fluorescence chromatograms of RFMS labeled fetuin N-glycans obtained with a DEAP HPCM 130Å 1.7μm 2.1 x 150 mm column under optimal conditions versus a GlycanPac AXR-1 2.1x150 mm column under identical and optimized conditions. Gradient changes are noted for each separation, include change in acetonitrile (MeCN) and change in buffer strength of ammonium formate/formic acid. Separation conditions are described in Example 12.

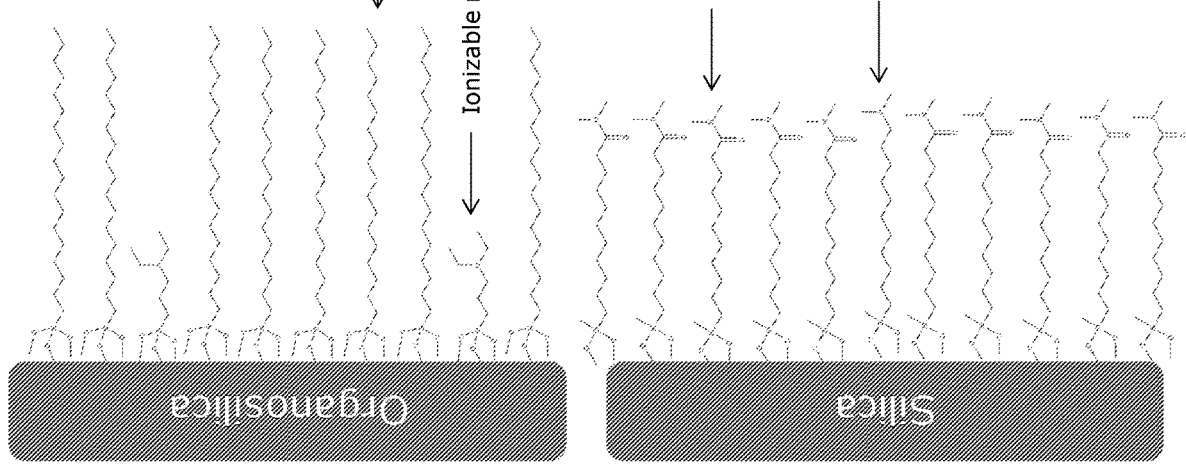
FIG. 16. Comparison example. (A) Representations of the DEAP HPCM material (DEAP HPCM, Phase 1A/1B) versus (B) Phase 21 of US patent application publication number US20140178912. Ratios of ionizable to neutral ligands is approximated schematically.

CHARGED SURFACE REVERSED PHASE CHROMATOGRAPHIC MATERIALS METHOD FOR ANALYSIS OF GLYCANS MODIFIED WITH AMPHIPATHIC, STRONGLY BASIC MOIETIES

CROSS-REFERENCE TO RELATED APPLICATIONS

This application is a national phase filing claiming the benefit of and priority to International Patent Application No. PCT/US2017/028856, filed on Apr. 21, 2017, which claims priority from and the benefit of U.S. Provisional Patent Application No. 62/326,783, filed on Apr. 24, 2016. The entire contents of these applications are incorporated herein by reference.

BACKGROUND OF THE INVENTION

Glycans are found throughout biological systems in both a free state as well as in conjugated forms as parts of glycoproteins, glycolipids, and proteoglycans. Glycans play a role in a variety of biological and physiological processes. Furthermore, the structures of glycans are diverse and complex. As a result, the full analysis of glycan profiles has been difficult.

Conventional HPLC chromatography has previously been utilized to analyze glycan profiles. These methods include reversed-phase chromatography, ion-exchange chromatography, and HILIC separations. Traditionally, released glycans have been separated by HILIC or, alternatively, by reversed phase chromatography using graphitic stationary phases, such as porous graphitized carbon, and mobile phases acidified by formic acid. (West, C.; Elfakir, C.; Lafosse, M., Porous graphitic carbon: a versatile stationary phase for liquid chromatography. *J Chromatogr A* 2010, 1217 (19), 3201-16; Ruhaak, L. R.; Zauner, G.; Huhn, C.; Bruggink, C.; Deelder, A. M.; Wuhrer, M., Glycan labeling strategies and their use in identification and quantification. *Anal Bioanal Chem* 2010, 397 (8), 3457-81.) However, these methods do not provide sufficient sensitivity to fully analyze glycans due to the hydrophilic and polar nature of glycans. In addition, many glycans that are labeled with moieties to increase method sensitivity are too strongly retained and insufficiently resolved.

Similarly, with reversed phase stationary phases bonded with C18, separations tend to produce problematic co-elutions, given that there is poor selectivity among glycan structures differing with respect to net charge. N-glycans that have been released from glycoproteins, such as human immunoglobulin G (hIgG), are quite different unto themselves. In particular, released N-glycans exhibit different charge characteristics than peptides, as they will generally contain only neutral or acidic hydrophilic residues. The acidic residues in released N-glycans, and their carboxylic acids or phospho groups, significantly impact the characteristic and net charge state of a glycan species. Glycans containing more acidic residues will have a more negative net charge. Similarly, these acidic species are often correlated with the efficacy of a biopharmaceutical, as is the case with epoetin and lysosomal disorder enzyme replacement therapies. (Lauber, M. A.; Koza, S. M.; McCall, S. A.; Alden, B. A.; Iraneta, P. C.; Fountain, K. J., High-Resolution Peptide Mapping Separations with MS-Friendly Mobile Phases and Charge-Surface-Modified C18. *Anal Chem* 2013, 85 (14), 6936-44; Bennett, C. L.; Spiegel, D. M.; Macdougall, I. C.; Norris, L.; Qureshi, Z. P.; Sartor, O.; Lai, S. Y.; Tallman, M. S.; Raisch, D. W.; Smith, S. W.; Silver, S.; Murday, A. S.; Armitage, J. O.; Goldsmith, D., A review of safety, efficacy, and utilization of erythropoietin, darbepoetin, and peginesatide for patients with cancer or chronic kidney disease: a report from the Southern Network on Adverse Reactions (SONAR). *Semin Thromb Hemost* 2012, 38 (8), 783-96).

New column technology, such as that described in United States Patent Publication No. 2013/0319086, has provided new multimodal chromatographic media and methods of analyzing glycans that provide high resolution between different biological macromolecules, unique selectivity based on size, composition, structure (e.g., isomerism, linkages), and/or charge. Furthermore, these columns allow the macromolecules eluted from the media to be detected by standard methodology (e.g., mass spectrometry, fluorescence detection) with no, or minimal, clean up or purification post-analysis and pre-detection (e.g., fluorescent tagging), this would greatly simplify and facilitate macromolecular analysis.

Nevertheless, such technology still does not provide sufficient sensitivity and selectivity for the complete separation of glycans, particularly N-glycans. Moreover, the same could be said for O-glycans. As such, there remains a need for alternative methods which provide that provide superior selectivity in analysis of glycans.

Fluorescent labeling of N-glycans is beneficial to detecting glycans because it improves both sensitivity and selectivity of the detection as well as the chromatographic behavior of glycans. Glycan analysis is important to pharmaceutical manufacturers as glycosylation profiling of proteins must be monitored to ensure consistency of a therapeutic product. Upon derivatization with a reagent having a fluorescent moiety, the identity of a glycan can be estimated. Mass spectrometry ("MS") is then required to identify the specific compound.

Analysis by MS has reached a high degree of development with respect to glycan and amino acid analysis and proteomics. The current state of the art utilizes tagging molecules that react quickly and give good MS/fluorescence signals. A combination of MS and fluorescence detection is desirable, however, because fluorescence detection is very useful tool in determining the relative quantities of different quantitatively how much is present. On the other hand, MS is used to determine what the molecular makeup is. The labels of choice for state-of-art glycan detection have tended to be unique in having relatively high hydrophobicity paired with a high pKa ionizable residue, making them so-called 'amphipathic, strongly basic' moieties.

A need exists, therefore, for chromatographic materials and corresponding separation methods that produce optimal selectivity and resolution for glycans labeled with amphipathic, strongly basic moieties.

SUMMARY OF THE INVENTION

The present invention provides novel methods for the chromatographic analysis of labeled glycans using high purity chromatographic materials (HPCMs) comprising a chromatographic surface wherein the chromatographic surface comprises a hydrophobic surface group and one or more ionizable modifier and a labeling reagent which is capable of providing amphipathic and strongly basic labeling moieties to a sample to be analyzed.

In one aspect, the invention provides a method for selectively isolating a glycan from a sample, the method comprising the steps of:

a) reacting a sample comprising a glycan with a labeling reagent to produce a labeled glycan sample b) loading the labeled glycan sample onto a chromatographic separation device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycan is selectively adsorbed onto the high purity chromatographic material; and c) eluting the adsorbed labeled glycan from the high purity chromatographic material, thereby selectively isolating the labeled glycan from the sample.

In another aspect, the invention provides a method for separating a plurality of glycans from a sample, the method comprising the steps of:

a) reacting a sample comprising a plurality of glycans with a labeling reagent to produce a labeled glycan sample b) loading the labeled glycan sample containing a plurality of glycans onto a chromatographic separation device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycans are adsorbed onto the high purity chromatographic material; and c) eluting the adsorbed labeled glycans from the high purity chromatographic material, thereby separating the labeled glycans.

In still another aspect, the invention provides a method for purifying a glycan contained in a sample, the method comprising:

a) reacting a sample comprising a glycan with a labeling reagent to produce a labeled glycan sample b) loading the labeled glycan sample onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycan are adsorbed onto the high purity chromatographic material; and c) eluting the adsorbed glycan from the high purity chromatographic material, thereby purifying the glycan.

In yet another aspect, the invention provides a method for detecting a glycan in a sample, the method comprising the steps of:

a) reacting a sample comprising a glycan with a labeling reagent to produce a labeled glycan sample a) loading the labeled glycan sample onto a chromatographic separation device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycans are adsorbed onto the high purity chromatographic material; and b) eluting the adsorbed glycan from the high purity chromatographic material; and c) detecting the glycan.

In certain embodiments, the glycan is an N-glycan or an O-glycan. In particular embodiments, the glycan is an hIgG glycan, a fetuin glycan, FA2BG2S2, FA2G2S1, or FA2G2.

In some embodiments the glycan labeling reagent is an MS-active, rapid fluorescence tagging compound; a procainamide reagent or a procaine reagent. In particular embodiments, the glycan labeling reagent provides an amphipatic, strongly basic moiety having a Log P value between 0 and 5; between 1 and 5; or between 1 and 3. In certain embodiments, the glycan labeling reagent provides an amphipatic, strongly basic moiety having a pKa value greater than 6; greater than 7; or greater than 8.

In particular embodiments, the glycan labeling reagent is a reagent having the formula:

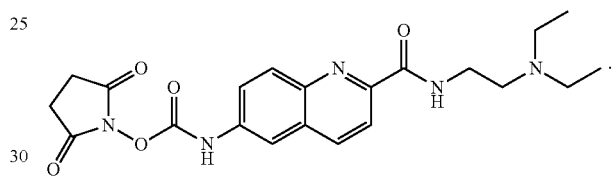

In some embodiments of the invention, the high purity chromatographic material further comprises a chromatographic core material.

In certain embodiments, the HPCMs of the invention comprise an ionizable modifier which contains a carboxylic acid group, a sulfonic acid group, an arylsulfonic group, a phosphoric acid group, a boronic acid group, an amino group, an imido group, an amido group, a pyridyl group, an imidazolyl group, an ureido group, a thionyl-ureido group, an amidino group, a guanidine group or an aminosilane group.

In still other embodiments, the ionizable modifier on the chromatographic surface is provided by reacting the chromatographic surface with an ionizable modifying reagent selected from groups having the formula (I)

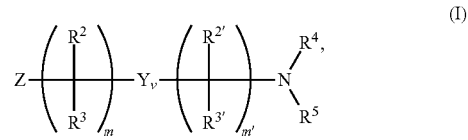

the formula (II):

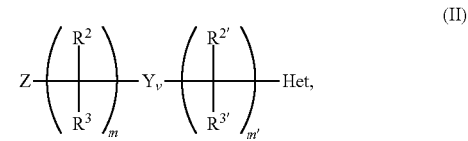

the formula (III):

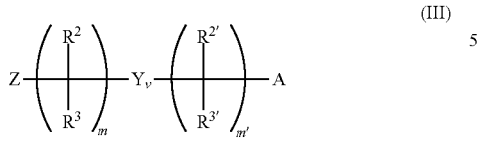

or a combination thereof
wherein
m is an integer from 1-8;
v is 0 or 1;
when v is 0, m' is 0;
when v is 1, m' is an integer from 1-8;
Z represents a chemically reactive group, including (but not limited to)

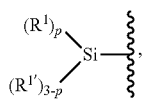

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;
Y is an embedded polar functionality;
each occurrence of R$^1$ independently represents a chemically reactive group on silicon, including (but not limited to) —H, —OH, —OR$^6$, dialkylamine, triflate, Br, Cl, I, vinyl, alkene, or —(CH$_2$)$_{m''}$Q;
each occurrence of Q is —OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;
m" is an integer from 1-8
p is an integer from 1-3;
each occurrence of R$^{1'}$ independently represents F, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, fluoroalkyl, or fluoroaryl;
each occurrence of R$^2$, R$^{2'}$, R$^3$ and R$^{3'}$ independently represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_2$-C$_{18}$ heterocycloalkyl, C$_5$-C$_{18}$ aryl, C$_5$-C$_{18}$ aryloxy, or C$_4$-C$_{18}$ heteroaryl, —Z, or a group having the formula —Si(R')$_b$R''$_a$ or —C(R')$_b$R''$_a$;
a and b each represents an integer from 0 to 3 provided that a+b=3;
R' represents a C$_1$-C$_6$ straight, cyclic or branched alkyl group;
R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety.
R$^4$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;
R$^5$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;
each occurrence of R$^6$ independently represents C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;
Het represents a heterocyclic or heteroaryl ring system comprising at least one nitrogen atom; and
A represents an acidic ionizable modifier moiety or a dual charge ionizable modifier moiety.

In still other embodiments, the ionizable modifying reagent is aminopropyltriethoxysilane, aminopropyltrimethoxysilane, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyl trichlorosilane, sulfopropyltrisilanol, carboxyethylsilanetriol, 2-(carbomethoxy)ethylmethyldichlorosilane, 2-(carbomethoxy) ethyltrichlorosilane, 2-(carbomethoxy) ethyltrimethoxysilane, n-(trimethoxysilylpropyl) ethylenediamine triacetic acid, (2-diethylphosphatoethyl) triethoxysilane, 3-mercaptopropyltriethoxysilane, 3-mercaptopropyltrimethoxysilane, bis[3-(triethoxysilyl)propyl]disulfide, bis[3-(triethoxysilyl)propyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl)trimethoxysilane, N-(hydroxyethyl)-N-methylaminopropyltrimethoxysilane, 3-(N,N-dimethylaminopropyl)trimethoxysilane, bis(2-hydroxyethyl)-3-aminopropyltriethoxysilane, N,N'-bis(hydroxyethyl)-N,N'-bis(trimethoxysilylpropyl) ethylenediamine, or N,N-dimethyl-3-aminopropylmethyldimethoxysilane.

In some embodiments, the hydrophobic surface group of the HPCM is a C4 to C30 bonded phase, an aromatic, a phenylalkyl, a fluoro-aromatic, a phenylhexyl, a pentafluorophenylalkyl, or a chiral bonded phase.

In other embodiments, the chromatographic core of the HPCM is a silica material or a hybrid inorganic/organic material.

In still other embodiments, the chromatographic core of the HPCM is a superficially porous material.

In certain embodiments, the high purity chromatographic material is a stationary phase prepared with a diethylaminoethyl, dimethylaminoethyl, dimethylaminopropyl, dimethylaminoethyl, or diethylaminopropyl (DEAP) modifier.

In still other embodiments, the elution step utilizes a mobile phase comprising a buffer solution having pH 1 to pH8; pH2 to pH7; or pH3 to pH6.

In other embodiments, the chromatographic separations device is a device is selected from the group consisting of a chromatographic column, a thin layer plate, a filtration membrane, a microfluidic separation device, a sample cleanup device, a solid support, a solid phase extraction device, a microchip separation device, and a microtiter plate.

In still other embodiments, the methods of the invention further comprise a step of treating the labeled glycan eluted in step c with a secondary chromatographic means to further isolate, purify, or separate the glycans. In particular such embodiments, the secondary chromatographic means is a second chromatographic separations device comprising a chromatographic material other than a high purity chromatographic material comprising a chromatographic surface wherein the chromatographic surface comprises a hydrophobic surface group and one or more ionizable modifiers, or a second chromatographic material in the chromatographic separations device other than a high purity chromatographic material comprising a chromatographic surface wherein the chromatographic surface comprises a hydrophobic surface group and one or more ionizable modifiers. In other particular embodiments, the secondary chromatographic separations device is a device is selected from the group consisting of a chromatographic column, a thin layer plate, a filtration membrane, a microfluidic separation device, a sample cleanup device, a solid support, a solid phase extraction device, a microchip separation device, and a microtiter plate.

Other embodiments of the methods of the invention; the labeling reagents and methods; and the synthesis and use of the HPCMs of the invention including hybrids, silica, particles, monoliths and superficially porous materials, are described in greater detail below.

BRIEF DESCRIPTION OF THE DRAWINGS

FIG. 1 depicts an exemplary chemical structure of a glycan modified with an amphipathic, strongly basic moiety; specifically, an RFMS labeled heptasaccharide glycan.

FIG. 2 depicts a fluorescence chromatogram resulting from the use of a Thermo Hypercarb 250 Å 3 µm 2.1×150 mm column and shows that labeled N-glycans of the invention are too strongly retained and inadequately resolved using a graphitic stationary phase. Separation conditions can be found in Example 2.

FIG. 3 depicts extracted ion chromatograms for labeled N-glycans of the invention (FA2G2, FA2G2S1, and FA2G2S2) resulting from the use of a conventional C18 reversed phase material and shows that the conventional separation provides insufficient selectivity as compared to the desired selectivity. Separation conditions are described in Example 2.

FIG. 4 depicts the fluorescence chromatogram resulting from the use of a Waters ACQUITY UPLC CSH C18 130 Å 1.7 µm 2.1×150 mm column showing that labeled N-glycans of the invention are retained and uniquely separated with high peak capacity using a charged surface reverse phase material. (A) depicts the full view whereas (B) depicts a zoomed view of the observed chromatographic peaks and their MS based assignments to neutral, monosialylated and desialylated glycans structures. Separation conditions are described in Example 3.

FIG. 5 depicts fluorescence chromatograms of hIgG glycans labeled in accordance with the invention showing the modulation of sensitivity, retentivity and selectivity through the use of various aqueous mobile phase additives. (A) Fluorescence chromatograms of labeled hIgG glycans separated with a Waters ACQUITY UPLC CSH C18 130 Å 1.7 µm 2.1×150 mm column and ammonium/formic acid based buffers. (B) Fluorescence chromatograms of labeled hIgG glycans separated with a Waters ACQUITY UPLC CSH C18 130 Å 1.7 µm 2.1×150 mm and ammonium formate/acetic acid based buffers. Separation conditions are described in Example 4.

FIG. 6 depicts fluorescence chromatograms of hIgG glycans labeled in accordance with the invention showing that constant ionic strength separations are advantageous for resolving highly sialylated glycans with HPCM. (A) Fluorescence chromatograms of labeled fetuin glycans separated with a Waters ACQUITY UPLC CSH C18 130 Å 1.7 µm 2.1×150 mm column and eluent mobile phases containing varying compositions of ammonium formate/acetic acid based buffers. 'MeCN' stands for acetonitrile. Separation conditions are described in Example 5.

FIG. 7 depicts fluorescence chromatograms of hIgG glycans labeled in accordance with the invention showing optimized separations using HPCM column chromatography. Fluorescence chromatograms of (A) labeled hIgG glycans and (B) labeled fetuin glycans as obtained with a Waters ACQUITY UPLC CSH C18 130 Å 1.7 µm 2.1×150 mm column. MS based identifications are provided. Separation conditions are described in Example 6.

FIG. 8 depicts fluorescence chromatograms of hIgG glycans labeled in accordance with the invention showing that a charged surface reversed phase material with a strongly basic, versus weakly basic, ionizable modifier requires different mobile phase optimization. Fluorescence chromatograms of labeled hIgG glycans as obtained with a DEAP HPCM 130 Å 1.7 µm 2.1×150 mm column. Mobile phases A and B and defined for each separation. 'MeCN' denotes acetonitrile. Separation conditions are described in Example 7.

FIG. 9 depicts fluorescence chromatograms of hIgG glycans labeled in accordance with the invention utilizing gradient conditions. Fluorescence chromatograms of labeled hIgG glycans as obtained with a DEAP HPCM 130 Å 1.7 µm 2.1×150 mm column. Gradient conditions are defined for each separation. Separation conditions are described in Example 8.

FIG. 10 depicts fluorescence chromatograms of hIgG glycans labeled in accordance with the invention utilizing a diethylaminopropyl (DEAP) modified HPCM chromatography column. Fluorescence chromatograms of (A) labeled hIgG glycans and (B) labeled fetuin glycans as obtained with a DEAP HPCM 130 Å 1.7 µm 2.1×150 mm column. MS based identifications are provided. Asterisks mark non-glycan peaks. Separation conditions are described in Example 9.

FIG. 11 depicts fluorescence chromatograms of hIgG glycans labeled in accordance with the invention utilizing a diethylaminopropyl (DEAP) modified HPCM chromatography column showing the improved separation of labeled glycans through adjustment of initial conditions to an ionic strength between 0 and 10 mM ammonium formate/formic acid buffer. Fluorescence chromatograms of labeled hIgG glycans obtained with a DEAP HPCM 130 Å 1.7 µm 2.1×150 mm column and different ionic strengths for initial conditions: 0, 5 and 10 mM ammonium formate/formic acid buffer. Gradient conditions are provided. 'MeCN' denotes acetonitrile. Separation conditions are described in Example 10.

FIG. 12 depicts fluorescence and base-peak intensity (BPI) chromatographs of glycans labeled in accordance with the invention utilizing a diethylaminopropyl (DEAP) modified HPCM chromatography column showing the improved separation showing support for high sensitivity ESI+MS detection. (A) Fluorescence and base peak intensity (BPI) chromatograms of labeled bovine fetuin glycans obtained with a DEAP HPCM 130 Å 1.7 µm 2.1×150 mm column and optimal method conditions. (B) A high signal-to-noise, low background ESI+ mass spectrum corresponding to the labeled glycan eluting at the marked retention time. Separation conditions are described in Example 9.

FIG. 13 depicts fluorescence chromatographs of glycans labeled in accordance with the invention utilizing a diethylaminopropyl (DEAP) modified HPCM chromatography column showing the improved separation of released fetuin glycans labeled with various amphipathic, strongly basic moieties. Fluorescence chromatograms of (A) RFMS labeled, (B) procaine labeled, and (C) procainamide labeled fetuin N-glycans as obtained with a DEAP HPCM 130 Å 1.7 m (Phase 1A) 2.1×150 mm column. Separation conditions are described in Example 11.

FIG. 14 depicts fluorescence chromatographs of hIgG glycans labeled in accordance with the invention utilizing a diethylaminopropyl (DEAP) modified HPCM chromatography column as compared to a commercially available m mixed-mode column. Separation conditions are described in Example 12.

FIG. 15 depicts fluorescence chromatographs of fetuin N-glycans labeled in accordance with the invention utilizing a diethylaminopropyl (DEAP) modified HPCM chromatography column as compared to a commercially available m mixed-mode column. Separation conditions are described in Example 12.

FIG. 16 depicts Representations of (A) the charged surface reverse phase material (DEAP HPCM, Phase 1A/1B) versus (B) Phase 21 of US patent application publication number US20140178912. Ratios of ionizable to neutral ligands is approximated schematically.

DETAILED DESCRIPTION OF THE INVENTION

The present invention provides novel chromatographic materials, e.g., for chromatographic separations, processes for their preparation; separations devices containing the chromatographic material; and methods of use thereof. The present invention will be more fully illustrated by reference to the definitions set forth below.

Definitions

"High Purity" or "high purity chromatographic material" includes a material which is prepared form high purity precursors. In certain aspects, high purity materials have reduced metal contamination and/or non-diminished chromatographic properties including, but not limited to, the acidity of surface silanols and the heterogeneity of the surface.

"Chromatographic surface" includes a surface which provides for chromatographic separation of a sample. In certain aspects, the chromatographic surface is porous. In some aspects, a chromatographic surface may be the surface of a particle, a superficially porous material or a monolith. In certain aspects, the chromatographic surface is composed of the surface of one or more particles, superficially porous materials or monoliths used in combination during a chromatographic separation. In certain other aspects, the chromatographic surface is non-porous.

"Ionizable modifier" includes a functional group which bears an electron donating or electron withdrawing group. In certain aspects, the ionizable modifier contains one or more carboxylic acid groups, amino groups, imido groups, amido groups, pyridyl groups, imidazolyl groups, ureido groups, thionyl-ureido groups, amidino groups, guanidine groups or aminosilane groups, or a combination thereof. In other aspects, the ionizable modifier contains a group bearing a nitrogen or phosphorous atom having a free electron lone pair. In certain aspects, the ionizable modifier is covalently attached to the material surface and has an ionizable group. In some instances it is attached to the chromatographic material by chemical modification of a surface hybrid group.

"Hydrophobic surface group" includes a surface group on the chromatographic surface which exhibits hydrophobicity. In certain aspects, a hydrophobic group can be a carbon bonded phase such as a C4 to C18 bonded phase. In other aspects, a hydrophobic surface group can contain an embedded polar group such that the external portion of the hydrophobic surface maintains hydrophobicity. In some instances it is an attached to the chromatographic material by chemical modification of a surface hybrid group. In other instances the hydrophobic group can be C4-C30, embedded polar, chiral, phenylalkyl, or pentafluorophenyl bonding and coatings.

"Chromatographic core" includes a chromatographic materials, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material may be disposed on or bonded to or annealed to the chromatographic core in such a way that a discrete or distinct transition is discernable or may be bound to the chromatographic core in such a way as to blend with the surface of the chromatographic core resulting in a gradation of materials and no discrete internal core surface. In certain embodiments, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability "Hybrid", including "hybrid inorganic/organic material," includes inorganic-based structures wherein an organic functionality is integral to both the internal or "skeletal" inorganic structure as well as the hybrid material surface. The inorganic portion of the hybrid material may be, e.g., alumina, silica, titanium, cerium, or zirconium or oxides thereof, or ceramic material. "Hybrid" includes inorganic-based structures wherein an organic functionality is integral to both the internal or "skeletal" inorganic structure as well as the hybrid material surface. As noted above, exemplary hybrid materials are shown in U.S. Pat. Nos. 4,017,528, 6,528,167, 6,686,035 and 7,175,913.

The term "alicyclic group" includes closed ring structures of three or more carbon atoms. Alicyclic groups include cycloparaffins or naphthenes which are saturated cyclic hydrocarbons, cycloolefins, which are unsaturated with two or more double bonds, and cycloacetylenes which have a triple bond. They do not include aromatic groups. Examples of cycloparaffins include cyclopropane, cyclohexane and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —CF3, —CN, or the like.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl and the like. As used herein, the term "nitro" means —NO2; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., C1-C30 for straight chain or C3-C30 for branched chain. In certain embodiments, a straight chain or branched chain alkyl has 20 or fewer carbon atoms in its backbone, e.g., C1-C20 for straight chain or C3-C20 for branched chain, and more preferably 18 or fewer. Likewise, preferred cycloalkyls have from 4-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and Claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of Ra and Rb, is further substituted with an amino group.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF3, —CN, or the like.

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "ceramic precursor" is intended include any compound that results in the formation of a ceramic material.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

The term "embedded polar functionality" is a functionality that provides an integral polar moiety such that the interaction with basic samples due to shielding of the unreacted silanol groups on the silica surface is reduced. Embedded polar functionalities include, but are not limited to carbonate, amide, urea, ether, thioether, sulfinyl, sulfoxide, sulfonyl, thiourea, thiocarbonate, thiocarbamate, ethylene glycol, heterocyclic, triazole functionalities or carbamate functionalities such as disclosed in U.S. Pat. No. 5,374,755, and chiral moieties.

The language "chromatographically-enhancing pore geometry" includes the geometry of the pore configuration of the presently-disclosed materials, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced", e.g., as compared to a geometry known or conventionally used in the art. Examples of these factors include high separation efficiency, longer column life and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid materials is distinguished from the prior art materials by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid materials containing only a small population of micropores. A small population of micropores is achieved in hybrid materials when all pores of a diameter of about <34 Å contribute less than about 110 m$^2$/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 Å, determined by multipoint nitrogen sorption analysis from the adsorption leg of the isotherm using the BJH method. As used herein, the acronyms "MSA" and "MPA" are used interchangeably to denote "micropore surface area".

The term "functionalizing group" includes organic functional groups which impart a certain chromatographic functionality to a chromatographic stationary phase.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF3, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "metal oxide precursor" is intended include any compound that contains a metal and results in the formation of a metal oxide, e.g., alumina, silica, titanium oxide, zirconium oxide.

The term "monolith" is intended to include a collection of individual particles packed into a bed formation, in which the shape and morphology of the individual particles are maintained. The particles are advantageously packed using a material that binds the particles together. Any number of binding materials that are well known in the art can be used such as, for example, linear or cross-linked polymers of divinylbenzene, methacrylate, urethanes, alkenes, alkynes, amines, amides, isocyanates, or epoxy groups, as well as condensation reactions of organoalkoxysilanes, tetraalkoxysilanes, polyorganoalkoxysiloxanes, polyethoxysiloxanes, and ceramic precursors. In certain embodiments, the term "monolith" also includes hybrid monoliths made by other methods, such as hybrid monoliths detailed in U.S. Pat. No. 7,250,214; hybrid monoliths prepared from the condensation of one or more monomers that contain 0-99 mole percent silica (e.g., SiO$_2$); hybrid monoliths prepared from coalesced porous inorganic/organic particles; hybrid monoliths that have a chromatographically-enhancing pore geometry; hybrid monoliths that do not have a chromatographically-enhancing pore geometry; hybrid monoliths that have ordered pore structure; hybrid monoliths that have non-periodic pore structure; hybrid monoliths that have non-crystalline or amorphous molecular ordering; hybrid monoliths that have crystalline domains or regions; hybrid monoliths with a variety of different macropore and mesopore properties; and hybrid monoliths in a variety of different aspect ratios. In certain embodiments, the term "monolith" also includes inorganic monoliths, such as those described in G. Guiochon/*J. Chromatogr. A* 1168 (2007) 101-168.

The term "nanoparticle" is a microscopic particle/grain or microscopic member of a powder/nanopowder with at least one dimension less than about 100 nm, e.g., a diameter or particle thickness of less than about 100 nm (0.1 mm), which may be crystalline or noncrystalline. Nanoparticles have properties different from, and often superior to those of conventional bulk materials including, for example, greater strength, hardness, ductility, sinterability, and greater reactivity among others. Considerable scientific study continues to be devoted to determining the properties of nanomaterials, small amounts of which have been synthesized (mainly as nano-size powders) by a number of processes including colloidal precipitation, mechanical grinding, and gas-phase nucleation and growth. Extensive reviews have documented recent developments in nano-phase materials, and are incorporated herein by reference thereto: Gleiter, H. (1989) "Nano-crystalline materials," Prog. Mater. Sci. 33:223-315 and Siegel, R. W. (1993) "Synthesis and properties of nano-phase materials," Mater. Sci. Eng. A 168:189-197. In certain embodiments, the nanoparticles comprise oxides or nitrides of the following: silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, and mixtures thereof. In certain embodiments, the nanoparticles of the present invention are selected from diamonds, zirconium oxide (amorphous, monoclinic, tetragonal and cubic forms), titanium oxide (amorphous, anatase, brookite and rutile forms), aluminum (amorphous, alpha, and gamma forms), and boronitride (cubic form). In particular embodiments, the nanoparticles of the present invention are selected from nano-diamonds, silicon carbide, titanium dioxide (anatase form), cubic-boronitride, and any combination thereof. Moreover, in particular embodiments, the nanoparticles may be crystalline or amorphous. In particular embodiments, the nanoparticles are less than or equal to 100 mm in diameter, e.g., less than or equal to 50 mm in diameter, e.g., less than or equal to 20 mm in diameter.

Moreover, it should be understood that the nanoparticles that are characterized as dispersed within the composites of the invention are intended to describe exogenously added nanoparticles. This is in contrast to nanoparticles, or formations containing significant similarity with putative nanoparticles, that are capable of formation in situ, wherein, for example, macromolecular structures, such as particles, may comprise an aggregation of these endogenously created.

The term "substantially disordered" refers to a lack of pore ordering based on x-ray powder diffraction analysis. Specifically, "substantially disordered" is defined by the lack of a peak at a diffraction angle that corresponds to a d value (or d-spacing) of at least 1 nm in an x-ray diffraction pattern.

"Surface modifiers" include (typically) organic functional groups which impart a certain chromatographic functionality to a chromatographic stationary phase. The porous inorganic/organic hybrid materials possess both organic groups and silanol groups which may additionally be substituted or derivatized with a surface modifier.

The language "surface modified" is used herein to describe the composite material of the present invention that possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later cross-linking, imparting the chemical character of the surface modifier to the base material. In one embodiment, the organic groups of a hybrid material, react to form an organic covalent bond with a surface modifier. The modifiers can form an organic covalent bond to the material's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds. A variety of synthetic transformations are well known in the literature, see, e.g., March, J. *Advanced Organic Chemistry*, 3rd Edition, Wiley, New York, 1985.

The term "mother sample" includes any sample including one or more glycans, including, but not limited to, a sample derived from a biological fluid selected from the group consisting of blood, urine, spinal fluid, synovial fluid, sputum, semen, saliva, tears, gastric juices and extracts and/or dilutions/solutions thereof, which is subjected to chromatographic or other separation means prior to obtain a sample for isolation, separation, purification, or detection by the materials and methods of the invention.

The term "Chromatographic separations device" includes any device capable of performing a chromatographic separation, including, but not limited to, a chromatographic column, a thin layer plate, a filtration membrane, a microfluidic separation device, a sample cleanup device, a solid support, a solid phase extraction device, a microchip separation device, and a microtiter plate.

The term "secondary chromatographic separations means" includes chromatographic separations devices and chromatographic materials comprised by chromatographic separation devices. In certain embodiments, a secondary chromatographic separations means is a separate or additional chromatographic separation device than the chromatographic separations device utilized in the methods of the invention. In other embodiments, the secondary chromatographic separations means is a separate or additional chromatographic material housed by the same chromatographic separations device utilized in the methods of the invention.

Chromatographic Surface/Stationary Phase Materials

The invention provides, a high purity chromatographic material (HPCM) comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety.

In certain aspects the HPCM may further comprise a chromatographic core material. In some aspects, the chromatographic core is a silica material; a hybrid inorganic/organic material; a superficially porous material; or a superficially porous particle. The chromatographic core material may be in the form of discrete particles or may be a monolith. The chromatographic core material may be any porous material and may be commercially available or may be produced by known methods, such as those methods described in, for example, in U.S. Pat. Nos. 4,017,528, 6,528,167, 6,686,035 and 7,175,913. In some embodiments, the chromatographic core material may be a non-porous core.

The composition of the chromatographic surface material and the chromatographic core material (if present) may be varied by one of ordinary skill in the art to provide enhanced chromatographic selectivity, enhanced column chemical stability, enhanced column efficiency, and/or enhanced mechanical strength. Similarly, the composition of the surrounding material provides a change in hydrophilic/lipophilic balance (HLB), surface charge (e.g., isoelectric point or silanol pKa), and/or surface functionality for enhanced chromatographic separation. Furthermore, in some embodiments, the composition of the chromatographic material may also provide a surface functionality for available for further surface modification.

The ionizable modifiers and the hydrophobic surface groups of the HPCMs of the invention can be prepared using known methods. Some of the ionizable modifier reagents are commercially available. For example silanes having amino alkyl trialkoxysilanes, methyl amino alkyl trialkoxysilanes, and pyridyl alkyl trialkoxysilanes are commercially available. Other silanes such as chloropropyl alkyl trichlorosilane and chloropropyl alkyl trialkoxysilane are also commercially available. These can be bonded and reacted with imidazole to create imidazolyl alkyl silyl surface species, or bonded and reacted with pyridine to create pyridyl alkyl silyl surface species. Other acidic modifiers are also commercially available, including, but not limited to, sulfopropyl-trisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine, triacetic acid, (2-diethylphosphatoethyl)triethoxysilane, 2-(chlorosulfonylphenyl)ethyltrichlorosilane, and 2-(chlorosulfonylphenyl)ethyltrimethoxysilane.

It is known to one skilled in the art to synthesize these types of silanes using common synthetic protocols, including Grinard reactions and hydrosilylations. Products can be purified by chromatography, recrystallization or distillation Other additives such as isocyanates are also commercially available or can be synthesized by one skilled in the art. A common isocyanate forming protocol is the reaction of a primary amine with phosgene or a reagent known as Triphosgene.

In some embodiments the ionizable modifier contains a carboxylic acid group, a sulfonic acid group, a phosphoric acid group, a boronic acid group, an amino group, an imido group, an amido group, a pyridyl group, an imidazolyl group, an ureido group, a thionyl-ureido group, an amidino group, a guanidine group, or an aminosilane group.

In other aspects the ionizable modifier reagent may be selected from groups formula (I)

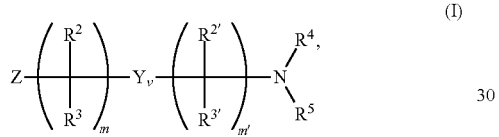
(I)

the formula (II):

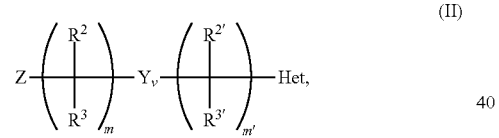
(II)

the formula (III):

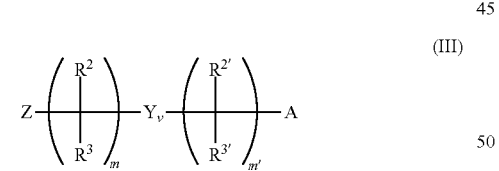
(III)

wherein
  m is an integer from 1-8;
  v is 0 or 1;
  when v is 0, m' is 0;
  when v is 1, m' is an integer from 1-8;
  Z represents a chemically reactive group, including (but not limited to)

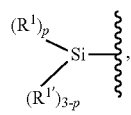

—OH, —$OR^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

Y is an embedded polar functionality;

each occurrence of $R^1$ independently represents a chemically reactive group on silicon, including (but not limited to) —H, —OH, —$OR^6$, dialkylamine, triflate, Br, Cl, I, vinyl, alkene, or —$(CH_2)_{m''}Q$;

each occurrence of Q is —OH, —$OR^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

m" is an integer from 1-8 p is an integer from 1-3;

each occurrence of $R^{1'}$ independently represents F, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, fluoroalkyl, or fluoroaryl;

each occurrence of $R^2$, $R^{2'}$, $R^3$ and $R^{3'}$ independently represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_2$-$C_{18}$ heterocycloalkyl, $C_5$-$C_{18}$ aryl, $C_5$-$C_{18}$ aryloxy, or $C_4$-$C_{18}$ heteroaryl, —Z, or a group having the formula —$Si(R')_b R''_a$ or —$C(R')_b R''_a$;

a and b each represents an integer from 0 to 3 provided that a+b=3;

R' represents a $C_1$-$C_6$ straight, cyclic or branched alkyl group;

R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety.

$R^4$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

$R^5$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

each occurrence of $R^6$ independently represents $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

Het represents a heterocyclic or heteroaryl ring system comprising at least one nitrogen atom; and A represents an acidic ionizable modifier moiety or a dual charge ionizable modifier moiety.

In yet other embodiments, the inoizable modifier is aminopropyltriethoxysilane, aminopropyltrimethoxysilane, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyl trichlorosilane, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine triacetic acid, (2-diethylphosphatoethyl)triethoxysilane, 3-mercaptopropyltriethoxysilane, 3-mercaptopropyltrimethoxysilane, bis[3-(triethoxysilyl)propyl]disulfide, bis[3-(triethoxysilyl)propyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl)trimethoxysilane, N-(hydroxyethyl)-N-methylaminopropyltrimethoxysilane, 3-(N,N-dimethylaminopropyl)trimethoxysilane, bis(2-hydroxyethyl)-3-aminopropyltriethoxysilane, N,N'-bis(hydroxyethyl)-N,N'-bis(trimethoxysilylpropyl)ethylenediamine, or N,N-dimethyl-3-aminopropylmethyldimethoxysilane.

In certain embodiments, when the ionizable modifier is of the formula (III), the acidic ionizable modifiers is a protected or deprotected forms of trisilanol, trialkoxysilane or trichlorosilane; or a salt of sulfonic acid alkyl silanes, sulfonic acid phenylalkyl silanes, sulfonic acid benzylalkyl silanes, sulfonic acid phenyl silanes, sulfonic acid benzyl silanes, carboxylic acid alkyl silanes, carboxylic acid phenylalkyl silanes, carboxylic acid benzylalkyl silanes, carboxylic acid phenyl silanes, carboxylic acid benzyl silanes, phosphoric acid alkyl silanes, phosphonic acid phenylalkyl silanes, phosphonic acid benzylalkyl silanes, phosphonic acid phenyl silanes, phosphonic acid benzyl silanes, boronic acid alkyl silanes, boronic acid phenylalkyl silanes, boronic acid benzylalkyl silanes, boronic acid phenyl silanes, boronic acid benzyl silanes.

In certain embodiments, when the ionizable modifier is of the formula (III), the acidic ionizable modifiers is a protected or deprotected version or a salt of sulfonic acid alkyl isocyanates, sulfonic acid phenylalkyl isocyanates, sulfonic acid benzylalkyl isocyanates, sulfonic acid phenyl isocyanates, sulfonic acid benzyl isocyanates carboxylic acid alkyl isocyanates, carboxylic acid phenylalkyl isocyanates, carboxylic acid benzylalkyl isocyanates, carboxylic acid phenyl isocyanates, carboxylic acid benzyl isocyanates, phosphoric acid alkyl isocyanates, phosphonic acid phenylalkyl isocyanates, phosphonic acid benzylalkyl isocyanates, phosphonic acid phenyl isocyanates, phosphonic acid benzyl isocyanates, boronic acid alkyl isocyanates, boronic acid phenylalkyl isocyanates, boronic acid benzylalkyl isocyanates, boronic acid phenyl isocyanates, or boronic acid benzyl isocyanates.

In certain embodiments, when the inoizable modifier reagent is selected from formula (III), A represents a dual charge ionizable modifier moiety. While not limited to theory; the dual charge ionizable modifier moiety has two sub-groups that can display opposite charges. Under some conditions the dual charge ionizable modifier moiety can act similarly to a zwitterions and ampholytes to display both a positive and negative charge and maintain a zero net charge. Under other conditions the dual charge ionizable modifier moiety may only have one group ionized and may display a net positive or negative charge. Dual charge ionizable modifier moieties include, but are not limited to, alkyl, branched alkyl, aryl, cyclic, polyaromatic, polycyclic, hertocyclic and polyheterocyclic groups that can display a positive charge (commonly on a nitrogen or oxygen atom), and a negative charge through an acidic group that includes a carboxylic, sulfonic, phosphonic or boronic acid. Alternatively, some metal containing complexes can display both positive and negative charges. Dual charge ionizable modifier moieties may also include, but are not limited to zwitterions, ampholyte, amino acid, aminoalkyl sulfonic acid, aminoalkyl carboxylic acid, mono and di-methylaminoalkyl sulfonic acid, mono and di-methylaminoalkyl carboxylic acid, pyridinium alkyl sulfonic acid, and pyridinium alkyl carboxylic acid groups. Alternatively the dual charge ionizable modifier moiety may be 2-(N-morpholino)ethanesulfonic acid, 3-(N-morpholino)propanesulfonic acid, 4-(2-hydroxyethyl)-1-piperazine ethanesulfonic acid), piperazine-N,N'-bis(2-ethanesulfonic acid), N-cyclohexyl-3-aminopropanesulfonic acid, N-cyclohexyl-2-hydroxyl-3-aminopropanesulfonic acid, 3-[(3-cholamidopropyl)dimethylammonio]-1-propanesulfonate, 6-Methyl-9,10-didehydro-ergoline-8-carboxylic acid, phenolsulfonphthalein, betaines, quinonoids, N,N-bis(2-hydroxyethyl)glycine, and N-[tris(hydroxymethyl)methyl]glycine groups.

Another aspect of this invention entails the use of a charged surface reversed phase material in which a HPCM weakly basic, ionizable modifier (pKa<7) is replaced with a strongly basic ionizable modifier (pKa>7). Without changing the coverage of the ionizable modifier, a charged surface reversed phase material with different physicochemical properties can thereby be obtained.

On exemplary stationary phase of this type utilizes a diethylaminoethyl, dimethylaminoethyl, dimethylaminopropyl, dimethylaminoethyl, or diethylaminopropyl (DEAP) modifier; C18 bonding; and subsequent endcapping (Example 1, Phase 1A).

In some embodiments, the ratio of the hydrophobic surface group: ionizable modifier in the HPCM of the invention is from about 4:1 to about 150:1; from about 20:1 to about 100:1; or from about 25:1 to about 100:1.

In other embodiments, the concentration of ionizable modifier in the HPCM of the invention is less than about 0.5 $\mu mol/m^2$; less than about 0.4 $\mu mol/m^2$; less than about 0.3 $\mu mol/m^2$; from about 0.01 $\mu mol/m^2$ to about 0.5 $\mu mol/m^2$; from about 0.1 $\mu mol/m^2$ to about 0.4 $\mu mol/m^2$; or from about 0.2 $\mu mol/m^2$ to about 0.3 $\mu mol/m^2$.

In still another aspect, the HPCM of the invention has a quantified surface coverage ratio, B/A, from about 2.5 to about 300 wherein A represents the ionizable modifier and B represents the hydrophobic group. In certain aspects, the quantified surface coverage ratio, B/A, is from about 3 to about 200, from about 4 to about 35 or from about 5 to about 22.

In another aspect, the hydrophobic surface group of the HPCM of the invention is a C4 to C18 bonded phase. In certain aspects, the hydrophobic surface group is a C18 bonded phase. In still other aspects, the hydrophobic surface group is an embedded polar bonded phase. In other aspects, the hydrophobic surface group is an aromatic, phenylalkyl, fluoro-aromatic, phenylhexyl, or pentafluorophenylalkyl bonded phase. In another aspect, the hydrophobic surface group is a $C_4$-$C_{30}$, embedded polar, chiral, phenylalkyl, or pentafluorophenyl bonding or coating.

In certain embodiments, the HPCM of the invention may be in the form of a particle, a monolith or a superficially porous material. In certain other aspects, the HPCM of the invention is a non-porous material.

In certain aspects, the HPCM of the invention may be an inorganic material (e.g., silica), a hybrid organic/inorganic material, an inorganic material (e.g., silica) with a hybrid surface layer, a hybrid particle with a inorganic (e.g., silica) surface layer, or a hybrid particle with a different hybrid surface layer.

In one embodiment, the HPCM of the invention does not have chromatographically enhancing pore geometry. In another embodiment, the HPCM of the invention has chromatographically enhancing pore geometry.

In certain embodiments, the HPCM of the invention has a surface area of about 25 to 1100 m$^2$/g; about 80 to 500 m$^2$/g; or about 120 to 330 m$^2$/g.

In other embodiments, the HPCM of the invention a pore volume of about 0.15 to 1.7 cm$^3$/g; or about 0.5 to 1.3 cm$^3$/g.

In certain other embodiments, the HPCM of the invention is non-porous.

In yet other embodiments, the HPCM of the invention has a micropore surface area of less than about 110 m$^2$/g; less than about 105 m$^2$/g; less than about 80 m$^2$/g; or less than about 50 m$^2$/g.

In still yet other embodiments, the HPCM of the invention has an average pore diameter of about 20 to 1500 Å; about 50 to 1000 Å; about 100 to 750 Å; or about 150 to 500 Å.

In another embodiment, the HPCM of the invention is hydrolytically stable at a pH of about 1 to about 14; at a pH of about 10 to about 14; or at a pH of about 1 to about 5.

In another aspect, the invention provides materials as described herein wherein the HPCM material further comprises a nanoparticle or a mixture of more than one nanoparticles dispersed within the chromatographic surface.

In certain embodiments, the nanoparticle is present in <20% by weight of the nanocomposite, <10% by weight of the nanocomposite, or <5% by weight of the nanocomposite.

In other embodiments, the nanoparticle is crystalline or amorphous and may be silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, or a nitride thereof. In particular embodiments, the nanoparticle is a substance which comprises one or more moieties selected from the group consisting of nano-diamonds, silicon carbide, titanium dioxide, and cubic-boronitride.

In other embodiments, the nanoparticles may be less than or equal to 200 nm in diameter, less than or equal to 100 nm in diameter, less than or equal to 50 nm in diameter, or less than or equal to 20 nm in diameter.

Surface Modification

The HPCM materials of the invention may further be surface modified.

Thus, in one embodiment, the material as described herein may be surface modified with a surface modifier having the formula $Z_a(R')_b$Si—R", where Z=Cl, Br, I, $C_1$-$C_5$ alkoxy, dialkylamino or trifluoromethanesulfonate; a and b are each an integer from 0 to 3 provided that a+b=3; $R^1$ is a $C_1$-$C_6$ straight, cyclic or branched alkyl group, and R" is a functionalizing group.

In another embodiment, the materials have been surface modified by coating with a polymer.

In certain embodiments, R' is selected from the group consisting of methyl, ethyl, propyl, isopropyl, butyl, t-butyl, sec-butyl, pentyl, isopentyl, hexyl and cyclohexyl. In other embodiments, R' is selected from the group consisting of alkyl, alkenyl, alkynyl, aryl, cyano, amino, diol, nitro, ester, a cation or anion exchange group, an alkyl or aryl group containing an embedded polar functionality and a chiral moiety. In certain embodiments, R' is selected from the group consisting of aromatic, phenylalkyl, fluoroaromatic, phenylhexyl, pentafluorophenylalkyl and chiral moieties.

In one embodiment, R" is a $C_1$-$C_{30}$ alkyl group. In a further embodiment, R" comprises a chiral moiety. In another further embodiment, R" is a $C_1$-$C_{20}$ alkyl group.

In certain embodiments, the surface modifier comprises an embedded polar functionality. In certain embodiments, such embedded polar functionality includes carbonate, amide, urea, ether, thioether, sulfinyl, sulfoxide, sulfonyl, thiourea, thiocarbonate, thiocarbamate, ethylene glycol, heterocyclic, or triazole functionalities. In other embodiments, such embedded polar functionality includes carbamate functionalities such as disclosed in U.S. Pat. No. 5,374,755, and chiral moieties. Such groups include those of the general formula

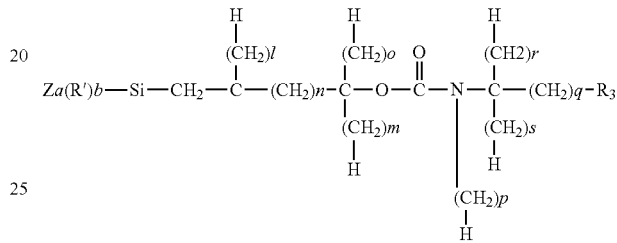

wherein 1, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

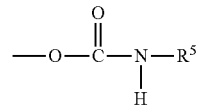

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

In certain embodiments, the surface modifier is selected from the group consisting of phenylhexyltrichlorosilane, pentafluorophenylpropyltrichlorosilane, octyltrichlorosilane, octadecyltrichlorosilane, octyldimethylchlorosilane and octadecyldimethylchlorosilane. In some embodiments, the surface modifier is selected from the group consisting of octyltrichlorosilane and octadecyltrichlorosilane. In other embodiments, the surface modifier is selected from the group consisting of an isocyanate or 1,1'-carbonyldiimidazole (particularly when the hybrid group contains a $(CH_2)_3OH$ group).

In another embodiment, the material has been surface modified by a combination of organic group and silanol group modification.

In still another embodiment, the material has been surface modified by a combination of organic group modification and coating with a polymer. In a further embodiment, the organic group comprises a chiral moiety.

In yet another embodiment, the material has been surface modified by a combination of silanol group modification and coating with a polymer.

In other embodiments, the material has been surface modified via formation of an organic covalent bond between the particle's organic group and the modifying reagent.

In still other embodiments, the material has been surface modified by a combination of organic group modification, silanol group modification and coating with a polymer.

In another embodiment, the material has been surface modified by silanol group modification.

In certain embodiments, the surface modified layer may be porous or non-porous.

Labeling Reagents and Moieties

Another aspect of the invention is the use of a labeling reagent which is capable of providing amphipathic and strongly basic labeling moieties to a sample to be analyzed.

A variety of labeling reagents may be used to provide the desired moieties for analysis and separation.

In certain embodiments, the glycan labeling reagent of the invention provides an amphipatic, strongly basic moiety having Log P values between 0 and 5; between 0 and 3; between 1 and 5; or between 1 and 3. In certain embodiments, the glycan labeling reagent of the invention provides an amphipatic, strongly basic moiety having pKa values greater than 6; greater than 7; or greater than 8.

In certain embodiments, the labeling reagent is an MS active, rapid fluorescence tagging compound which provides a moiety of the structural Formula:

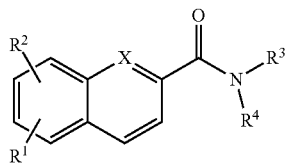

or a salt or solvate thereof, wherein
X=C or N;
R1 is independently selected from O=C=N—,

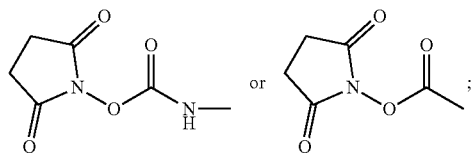

R2 is independently selected from —H, —C1-C8 alkyl, —C1-C8 cycloalkyl, halo, dialkylamino, CH2-dialkylamino, aminocarbonyl, alkoxycarbonyl, or alkoxy, but not Cl or O=C=N—; and
R3 and R4 are independently selected from —H, alkyl, alkyl amino, alkylsulfonic acid, alkyl phosphonic acid, wherein R3 or R4 is alkylamino, alkyl phosphonic acid, or alkylsulfonic acid, and wherein R3 and R4 together with the nitrogen to which they are attached may form an optionally substituted 5- to 8-membered saturated or partially unsaturated ring but not when R1 is O=C=N—.

The compounds of the formulas described herein may have optical centers and therefore may occur in different enantiomeric and disastereomeric configurations. The invention described herein includes all enantiomers, diastereomers and other stereoisomers of such compounds of each formula, as well as racemic compounds and racemic mixtures and other mixtures of stereoisomers thereof.

The compounds described herein may also form hydrogen bonds with other compounds. A hydrogen bond is an electromagnetic attractive interaction between polar molecules, where hydrogen is bonded to an electronegative atom such as nitrogen or oxygen. The hydrogen bond represents a strong dipole-dipole attraction. These hydrogen-bond attractions can occur between molecules (intermolecular) or within different parts of a single molecule (intramolecular). When a hydrogen atom is attached to an electronegative atom, it is considered a hydrogen bond donor. The electronegative atom is considered a hydrogen bond acceptor, whether it is bonded to a hydrogen atom or not.

Asymmetric centers exist in the compounds presented herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Hence, the compounds described herein can also be in the form of a salt or solvate, in particular acid addition salts. Through a reaction with either organic or inorganic acids, compounds presented herein or groups of compounds can form a salt. For example, in acid-base neutralization, an acid and a base react to form water and a salt. Basically, to react together, there must be the transfer of protons between acids and bases. Also, different acids can produce different ions. For example, an Arrhenius acid produces hydronium ions when it dissociates in water. Similarly, a Bronsted-Lowry acid is a proton donor that donates hydrogen ions to the base. Hence, proton acceptors and proton donors are the basis for the reaction and are referred to sometimes as a conjugate base or a conjugate acid. A conjugate pair refers to acids and bases with common features, where there is an equal loss/gain of protons between the pairs. For example NH4+ is the conjugate acid to the base NH3 because NH3 gains a hydrogen ion to form NH4+ as H2O donates a hydrogen ion to form OH—, the conjugate base. On the other hand, under a different theory, a Lewis acid accepts an electron pair and a Lewis base donates an electron pair donor. Accordingly, the proton H+ can be an electron pair acceptor. Moreover, a compound can be both, a Lewis acid and a Lewis base, depending on the reaction. For example, methyl iodide can behave as both, a Lewis acid and a Lewis base, where the methyl group is donated to form a salt.

Examples of acids which can be employed to form a salt of any of the compounds provided herein include inorganic acids and organic acids as well known to those skilled in the art such as, but not limited to, N-hydroxysuccinimide, hydrochloric, hydrofluoric, hydroiodic, hydrobromic, sulfuric, hydrosulfuric, thiosulfuric, hydrocyanic, phosphoric, phosphorous, hydrochlorous, chlorous, nitrous, nitric, chloric, perchloric, sulfurous, oxalic, maleic, succinic, and citric. Salts may also be formed by coordination of the compounds with an alkali metal or alkaline earth ion. In addition, other acids can form a salt including, but not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, isobutyric acid, lactic acid (DL), lactobionic acid, lauric acid, maleic acid, malic acid (−L), malonic acid, mandelic acid (DL), methanesulfonic acid, naphthalene-1,5, disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

For the compounds described herein, the counterion can be the conjugate base formed after reacting a compound or groups of compounds with an acid. In other words, counterion holds the opposite charge to that of the compound or compounds it is associated with. Thus, with respect to possible salts of the compounds herein having a conjugate acid of NH4+, the counterion represents the anionic part of the salt.

Hence, counterions of a salt compound described herein can include, but are not limited to, any of the following common anions and oxoanions: N-hydroxysuccinimidyl, hydride (H—), fluoride (F—), chloride (C—), bromide (Br—), iodide (I—), oxide (O2-), hydroxide (OH—), peroxide (O2 2-), sulfide (S2-), hydrogen sulfide (HS—), selenide (Se2-), nitride (N3-), azide (N3-), phosphide (P3-), arsinide (As3-), carbide (C4-), cyanide (CN—), hypochlorite (ClO1-), chlorite (ClO2-), chlorate (ClO3-), perchlorate (ClO4-), sulfite (SO3 2-), sulfate (SO4 2-), hydrogen sulfate (HSO4-), thiosulfate (S2O3 2-), nitrite (NO2-), nitrate (N3-), phosphite (PO3 2-), phosphate (PO4 3-), (mono)hydrogen phosphate (HPO4 2-), dihydrogen phosphate (H2PO4-), carbonate (CO3 2-), hydrogen carbonate (HCO3-), oxalate (C2O4 2-), cyanate (NCO—), isocyanate (OCN—), thiocyanate (SCN—), chromate (CrO4 2-), dichromate (Cr2O7 2-O), permanganate (MnO4-).

In certain embodiments, the glycan labeling reagent is a reagent having the formula:

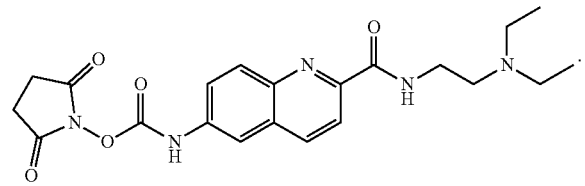 [SMILES: CCN(CC)CCNC(=O)c1ccc2cc(NC(=O)ON3C(=O)CCC3=O)ccc2n1]

In other embodiments, the labeling reagent is a procainamide or procaine reagent.

In other embodiments, the labeling reagent and their corresponding label moieties that are include, but not be limited to, labeling reagents and moieties described in U.S. patent application Ser. Nos. 14/342,131; 14/193,418, 14/458,760; and Ser. No. 15/005,619; and in U.S. Pat. Nos. 5,296,599; 7,148,069; 7,494,815; and 8, 124,792. The disclosures of each of these applications and patents are incorporated herein by reference in their entireties.

In certain embodiments, the labeling moiety is covalently bonded to the glycan through a secondary amine, urea, or amide linkage. In other embodiments, the labeling reagent can be applied to either an N-glycan or an O-glycan such that an amphipathic, strongly basic labeling moiety is incorporated and that the chromatographic methods described herein can be advantageously used.

Separation Devices and Kits

The HPCM materials described herein can be utilized in a variety of separation devices having a stationary phase comprising the HPCM materials. The separation devices include, e.g., chromatographic columns, thin layer plates, filtration membranes, sample cleanup devices and microtiter plates.

The HPCM materials impart to these devices improved lifetimes because of their improved stability.

Such devices include:
a) a column having a cylindrical interior for accepting a packing material, and
b) a packed chromatographic bed comprising the high purity chromatographic material as described herein.

Another such device includes a chromatographic device, comprising
a) an interior channel for accepting a packing material and
b) a packed chromatographic bed comprising the high purity chromatographic material as described herein.

The HPCM materials may also be utilized as a kit comprising the HPCM materials as described herein, and instructions for use. The kit may be for use with a separations device, e.g., chromatographic columns, thin layer plates, filtration membranes, sample cleanup devices and microtiter plates. In another embodiment, the instructions are for the separation, isolation, purification, or detection of one or more glycans.

Methods of Separation/Analysis

The invention provides methods for selectively isolating/separating, purifying, detecting and/or analyzing a glycan or mixture of glycans using the HPCM materials as described herein. In certain embodiments, the methods of the invention and the HPCM materials described herein may be utilized to selectively isolate/separate, purify, detect and/or analyze glycopeptides, glycoproteins, or glycolipids. The methods of the invention are capable of separating and thereby resolving complex mixtures of compounds, allowing rapid isolation/separation, purification, detection and/or analysis of component compounds of such mixtures.

In one aspect the invention provides a method for selectively isolating a glycan from a sample, the method comprising the steps of:
a) reacting a sample comprising a glycan with a labeling reagent to produce a labeled glycan sample
b) loading the labeled glycan sample onto a chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycan is selectively adsorbed onto the high purity chromatographic material; and c) eluting the adsorbed labeled glycan from the high purity chromatographic material, thereby selectively isolating the labeled glycan from the sample.

In still another aspect, the invention provides a method for separating a plurality of glycans from a sample, the method comprising the steps of:

a) reacting a sample comprising a plurality of glycans with a labeling reagent to produce a labeled glycan sample b) loading the labeled glycan sample containing a plurality of glycans onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycans are adsorbed onto the high purity chromatographic material; and c) eluting the adsorbed labeled glycans from the high purity chromatographic material, thereby separating the labeled glycans.

In yet another aspect, the invention provides a method for purifying a glycan contained in a sample, the method comprising the steps of:

a) reacting a sample comprising a glycan with a labeling reagent to produce a labeled glycan sample b) loading the labeled glycan sample onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycan are adsorbed onto the high purity chromatographic material; and c) eluting the adsorbed glycan from the high purity chromatographic material, thereby purifying the glycan.

In still yet another aspect, the invention provides a method for detecting a glycan in a sample, the method comprising the steps of:

a) reacting a sample comprising a glycan with a labeling reagent to produce a labeled glycan sample a) loading the labeled glycan sample onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the glycans are adsorbed onto the high purity chromatographic material; and b) eluting the adsorbed glycan from the high purity chromatographic material; and c) detecting the glycan.

In certain embodiments of the chromatographic methods of the invention, the glycan is an N-glycan or an O-glycan. In particular aspects, the glycan is an hIgG glycan, a fetuin glycan, FA2BG2S2, FA2G2S1, or FA2G2.

In certain embodiments the glycan labeling reagent is an MS-active, rapid fluorescence tagging compound; a procainamide reagent or a procaine reagent.

In certain other embodiments, the glycan labeling reagent is a reagent having the formula:

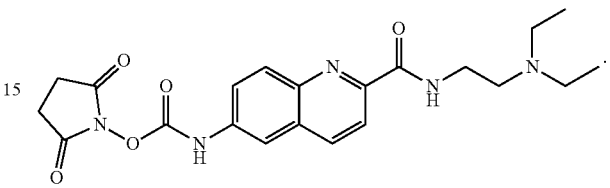

The methods of the invention can be used to selectively isolate, purify and/or detect glycans from a variety of samples. In one embodiment, the sample is or is derived from a biological fluid selected from the group consisting of blood, urine, spinal fluid, synovial fluid, sputum, semen, saliva, tears, gastric juices and extracts and/or dilutions/solutions thereof. In certain embodiments, the sample comprises a biological mixture of compounds.

In certain embodiments, the materials of the invention are found to produce significantly improved peak shape as compared to traditional chromatographic materials which do not utilize a charged surface. In another embodiment, the materials of the invention are found to produce advantageous selectivity by way of producing coulombic interactions between their charged surface and the same or opposite charges of analyte molecules. Furthermore, the materials of the invention are found to mitigate non-specific binding issues associated with traditional chromatographic materials which do not utilize a charged surface. Such benefits, in particular, allow for the identification or confirmation by mass spectrometry of low abundant macromolecules because they are not lost to non-specific binding and are not obscured by the degraded peak shapes that have been shown for abundant species, with traditional chromatographic materials, with the increase in sample mass needed to see the low abundant species.

In one aspect of this invention, the methods of the invention utilize a mobile phase in which separations coupled to ESI+MS detection yield high signal-to-noise mass spectra. Such mobile phases include, but are not limited to, mobile phases comprising buffer solutions having pH 1 to pH8; pH2 to pH7; or pH3 to pH6. The use of buffering additives in the aqueous mobile phase of the separation can significantly modulate MS sensitivity, retentivity and selectivity (FIG. 5).

In a particular embodiment, the aqueous mobile phase comprises a buffer solution of pH 3.6-1 mM ammonium formate/1 mM formic acid. This solution is effective in yielding separations that show high resolution isomer separation as well as some class separation driven by analyte charge state. Nevertheless, as also shown in FIG. 6, an aqueous mobile phase comprising 17 mM acetic acid and 1 mM ammonium formate is also effective.

In certain embodiments, the methods of the invention are performed under constant ionic strength conditions. This is evidenced in the separations of labeled glycans from bovine fetuin (FIG. 6). These glycans are unique in being highly sialylated and highly branched. Without any ionic strength in the eluent mobile phase, tetrasialylated labeled glycans would not be expected to be eluted from a column of the invention. Use of an additive in the eluent mobile phase, one that mirrors that of the aqueous mobile phase, facilitates the recovery of highly sialylated structures. As such, one embodiment of the invention utilizes the appropriate selection of additives along with optimization of gradient steepness. FIG. 7 shows these example separations wherein labeled glycans from hIgG and bovine fetuin are analyzed. The chromatogram obtained for labeled hIgG glycans is noteworthy in showing high resolution clustering of the so-called neutral N-glycan structures (afucosylated species and fucosylated species with or without a bisecting N-acetyl glucosamine) along with a high degree of resolution between and among the multiple mono- and di-sialylated N-glycan species (FIG. 7A). Meanwhile, the chromatogram obtained for labeled fetuin glycans (FIG. 7B) is notable for demonstrating that reasonable resolution can be obtained among glycans that contain three and four sialic acid residues.

In particular embodiments, the HPCM of the invention is a stationary phase prepared with a diethylaminoethyl, dimethylaminoethyl, dimethylaminopropyl, dimethylaminoethyl, or diethylaminopropyl (DEAP) modifier, including but not limited to a 1.7 μm, 130 Å average pore diameter material prepared from an organosilica particle, a diethylaminoethyl, dimethylaminoethyl, dimethylaminopropyl, dimethylaminoethyl, or diethylaminopropy (DEAP) modifier; C18 bonding; and subsequent endcapping. (Example 1, Phase 1A). This 'DEAP" material (Phase 1A, described in Example 1) has been evaluated for its ability to resolve glycans labeled with amphipathic, strongly basic moieties as described below.

In this regard, it has been found that this material produces a more pronounced class separation of glycans that differ by their net charge. As such, in another embodiment, the invention provides the analysis of labeled hIgG glycans with this DEAP stationary phase with simultaneous gradients that deliver increasing concentrations of both organic solvent and buffer (FIG. 8). The magnitude of ionic strength change that is needed for these separations may be defined via separations of labeled glycans prepared from both hIgG and bovine fetuin (FIG. 9). On a linear gradient from 0.5 to 32% acetonitrile (MeCN), these separations are optimized with a gradient from 0 to 100 mM ammonium formate and 100 mM formic acid. It is with this pairing of organic solvent and ionic strength change that there is good recovery of all glycan species and an optimal class separation of the glycans that differ by their extent of sialylation and consequently their net charge. Though not demonstrated here, it is envisioned that these sorts of gradients could be implemented with either a binary pump apparatus or even a ternary solvent delivery system. In addition, non-linear or multi-step gradients could be used to tune the separation for achieving differently selectivity and resolution.

Synthesis of Materials of the Invention

The invention also provides methods for producing the high purity chromatographic materials (HPCM) materials described herein.

In one embodiment, the invention provides a method for producing the HPCM described herein comprising the steps of:

a. reacting a chromatographic core with an ionizable modifying reagent to obtain a ionizable modified material; and
b. reacting the resultant material with a hydrophobic surface modifying group.

In another embodiment, the invention provides a method for producing the high purity chromatographic materials described herein comprising the steps of:

a. reacting a chromatographic core with hydrophobic surface modifying group to obtain a surface modified material; and
b. reacting the resultant material with an ionizable modifying reagent.

In another embodiment, the invention provides a method for producing the High purity chromatographic materials described herein comprising the steps of:

a. reacting a chromatographic core with hydrophobic surface modifying group to obtain a surface modified material; and
b. reacting the resultant material with an endcapping surface group, and
c. reacting the resultant material with an ionizable modifying reagent.

In another embodiment, the invention provides a method for producing the High purity chromatographic materials described here comprising the steps of:

a. reacting a chromatographic core with an ionizable modifying reagent to obtain an ionizable modified material; and
b. reacting the resultant material to produce a hybrid surface layer; and
c. reacting the resultant material with a hydrophobic surface modifying group.

In one aspect, the HPCM of the invention as described above is made with a charge ratio, $B'/A'$, from about 3 to about 133 wherein $A'$ represents the ionizable modifier reagent charged in the preparation and $B'$ represents the hydrophobic group charged in the preparation. In certain aspects, the charge ratio, $B'/A'$, is from about 4 to about 80, from about 4 to about 15, or from about 6 to about 7.

In one embodiment, the methods described herein further comprise the step of endcapping remaining silanol groups.

In one embodiment, in the methods described the steps are performed simultaneously.

In another embodiment, the pore structure of the as-prepared high purity chromatographic materials is modified by hydrothermal treatment, which enlarges the openings of the pores as well as the pore diameters, as confirmed by nitrogen ($N_2$) sorption analysis. The hydrothermal treatment is performed by preparing a slurry containing the as-prepared hybrid material and a solution of a base in water, heating the slurry in an autoclave at an elevated temperature, e.g., 100 to 200° C., for a period of 10 to 30 h. The use of an alkyl amine such as trimethylamine (TEA) or Tris(hydroxymethyl) methyl amine or the use of sodium hydroxide is advantageous. The thus-treated material is cooled, filtered and washed with water and methanol, then dried at 80° C. under reduced pressure for 16 h.

In certain embodiments, following hydrothermal treatment, the surfaces of the high purity chromatographic materials are modified with various agents. Such "surface modifiers" include (typically) organic functional groups which impart a certain chromatographic functionality to a chromatographic stationary phase. In certain aspects, when the HPCM is a hybrid material, it possesses possess both organic groups and silanol groups which may additionally be substituted or derivatized with a surface modifier.

The surface of the hydrothermally treated high purity chromatographic materials contains organic groups, which can be derivatized by reacting with a reagent that is reactive towards the materials' organic group. For example, vinyl groups on the material can be reacted with a variety of olefin reactive reagents such as bromine ($Br_2$), hydrogen ($H_2$), free radicals, propagating polymer radical centers, dienes and the like. In another example, hydroxyl groups on the material can be reacted with a variety of alcohol reactive reagents such as isocyanates, carboxylic acids, carboxylic acid chlorides and reactive organosilanes as described below. Reactions of this type are well known in the literature, see, e.g., March, J. *Advanced Organic Chemistry*, $3^{rd}$ Edition, Wiley, New York, 1985; Odian, G. The *Principles of Polymerization*, $2^{nd}$ Edition, Wiley, New York, 1981.

In addition, the surface of the hydrothermally treated high purity chromatographic materials also contains silanol groups, which can be derivatized by reacting with a reactive organosilane. The surface derivatization of the high purity chromatographic materials is conducted according to standard methods, for example by reaction with octadecyltrichlorosilane or octadecyldimethylchlorosilane in an organic solvent under reflux conditions. An organic solvent such as toluene is typically used for this reaction. An organic base such as pyridine or imidazole is added to the reaction mixture to catalyze the reaction. The product of this reaction is then washed with water, toluene and acetone. This material can be further treated by hydrolysis in a pH modified aqueous organic solution at ambient or elevated temperatures. An organic solvent such as acetone is typically used for this hydrolysis. Modification of pH can be achieved using acid or base modifiers, including trifluoroacetic acid, formic acid, hydrochloric acid, acetic acid, sodium or ammonium formate, sodium, potassium or ammonium acetate, phosphate buffers, ammonium hydroxide, ammonium carbonate, or ammonium bicarbonate. The product of the hydrolysis is then washed with water, toluene and acetone and dried at 80° C. to 100° C. under reduced pressure for 16 h. The resultant materials can be further reacted with a short-chain silane such as trimethylchlorosilane to endcap the remaining silanol groups, by using a similar procedure described above.

Surface modifiers such as disclosed herein are attached to the base material, e.g., via derivatization or coating and later crosslinking, imparting the chemical character of the surface modifier to the base material. In one embodiment, the organic groups of the high purity chromatographic materials react to form an organic covalent bond with a surface modifier. The modifiers can form an organic covalent bond to the materials organic group via a number of mechanisms well known in organic and polymer chemistry including but not limited to nucleophilic, electrophilic, cycloaddition, free-radical, carbene, nitrene and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur and the halogens. In addition, carbon-silicon and carbon-oxygen-silicon bonds are defined as organic covalent bonds, whereas silicon-oxygen-silicon bonds that are not defined as organic covalent bonds.

The term "functionalizing group" includes organic functional groups which impart a certain chromatographic functionality to a chromatographic stationary phase, including, e.g., octadecyl ($C_{18}$) or phenyl. Such functionalizing groups are incorporated into base material directly, or present in, e.g., surface modifiers such as disclosed herein which are attached to the base material, e.g., via derivatization or coating and later crosslinking, imparting the chemical character of the surface modifier to the base material.

In certain embodiments, silanol groups are surface modified. In other embodiments, organic groups are surface modified. In still other embodiments, the high purity chromatographic materials' organic groups and silanol groups are both surface modified or derivatized. In another embodiment, the high purity chromatographic materials are surface modified by coating with a polymer. In certain embodiments, surface modification by coating with a polymer is used in conjunction with silanol group modification, organic group modification, or both silanol and organic group modification. The ionizable modifier may be added to the material by silanol group modification, organic group modification, or by both silanol and organic group modification. The hydrophobic surface group may be added to the material by silanol group modification, organic group modification, or by both silanol and organic group modification.

More generally, the surface of high purity chromatographic materials may be modified by: treatment with surface modifiers including compounds of formula $Z_a(R')_b Si$—R", where Z=Cl, Br, I, $C_1$-$C_5$ alkoxy, dialkylamino, e.g., dimethylamino, or trifluoromethanesulfonate; a and b are each an integer from 0 to 3 provided that a+b=3; R' is a $C_1$-$C_6$ straight, cyclic or branched alkyl group, and R" is a functionalizing group. In certain instances, such materials have been surface modified by coating with a polymer.

R' includes, e.g., methyl, ethyl, propyl, isopropyl, butyl, t-butyl, sec-butyl, pentyl, isopentyl, hexyl or cyclohexyl; preferably, R' is methyl.

The functionalizing group R" may include alkyl, alkenyl, alkynyl, aryl, cyano, amino, diol, nitro, ester, cation or anion exchange groups, an alkyl or aryl group containing an embedded polar functionalities or chiral moieties. Examples of suitable R" functionalizing groups include chiral moieties, $C_1$-$C_{30}$ alkyl, including $C_1$-$C_{20}$, such as octyl ($C_8$), octadecyl ($C_{18}$) and triacontyl ($C_{30}$); alkaryl, e.g., $C_1$-$C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate, amide, urea, ether, thioether, sulfinyl, sulfoxide, sulfonyl, thiourea, thiocarbonate, thiocarbamate, ethylene glycol, heterocyclic, and triazole functionalities or carbamate functionalities such as disclosed in U.S. Pat. No. 5,374,755, and chiral moieties. In certain embodiments, R" is selected from the group consisting of aromatic, phenylalkyl, fluoroaromatic, phenylhexyl, pentafluorophenylalkyl and chiral moieties. Such groups include those of the general formula

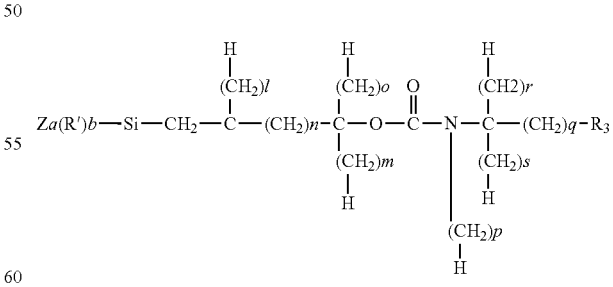

wherein l, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

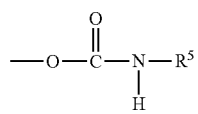

wherein R[5] may be, e.g., cyanoalkyl, t-butyl, butyl, octyl, dodecyl, tetradecyl, octadecyl, or benzyl. Advantageously, R[5] is octyl, dodecyl, or octadecyl.

In certain applications, such as chiral separations, the inclusion of a chiral moiety as a functionalizing group is particularly advantageous.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III) and chemisorption of presynthesized polymers onto the surface of the support (type IV). see, e.g., Hanson, et al., *J. Chromat.* A656 (1993) 369-380, the text of which is incorporated herein by reference. As noted above, coating the hybrid material with a polymer may be used in conjunction with various surface modifications described in the invention.

Thus, in certain embodiments, the hydrophobic surface modifier is selected from the group consisting of phenyl-hexyltrichlorosilane, pentafluorophenylpropyltrichlorosilane, octyltrichlorosilane, octadecyltrichlorosilane, octyldimethylchlorosilane and octadecyldimethylchlorosilane. In a further embodiment, the surface modifier is selected from the group consisting of octyltrichlorosilane and octadecyltrichlorosilane.

In another embodiment, the high purity chromatographic materials have been surface modified by a combination of organic group and silanol group modification.

In other embodiments, the high purity chromatographic materials have been surface modified by a combination of organic group modification and coating with a polymer.

In other embodiments, the high purity chromatographic materials have been surface modified by a combination of silanol group modification and coating with a polymer.

In another embodiment, the high purity chromatographic materials have been surface modified via formation of an organic covalent bond between the hybrid cores' and/or surrounding material materials' organic group and the modifying reagent.

In certain embodiments, the high purity chromatographic materials have been surface modified by a combination of organic group modification, silanol group modification and coating with a polymer.

In one embodiment, the high purity chromatographic materials have been surface modified by silanol group modification.

In another embodiment, the invention provides a method wherein the high purity chromatographic materials are modified by further including a porogen. In a further embodiment, the porogen is selected from the group consisting of cyclohexanol, toluene, mesitylene, 2-ethylhexanoic acid, dibutylphthalate, 1-methyl-2-pyrrolidinone, 1-dodecanol and Triton X-45. In certain embodiments, the porogen is toluene or mesitylene.

In one embodiment, the invention provides a method wherein the high purity chromatographic materials are further modified by including a surfactant or stabilizer. In certain embodiments, the surfactant is Triton X-45, Triton X100, Triton X305, TLS, Pluronic F-87, Pluronic P-105, Pluronic P-123, sodium dodecylsulfate (SDS), ammonia docecylsulfate, TRIS docecylsulfate, or Triton X-165. In certain embodiments, the surfactant is sodium dodecylsulfate (SDS), ammonia docecylsulfate, or TRIS docecylsulfate.

Certain embodiments of the synthesis of the HPCMs of the invention including hybrids, silica, particles, monoliths and superficially porous materials, as described above are further illustrated in the Examples below.

EXAMPLES

The present invention may be further illustrated by the following non-limiting examples describing the surface modification of porous chromatographic materials.

Materials

All reagents were used as received unless otherwise noted. Those skilled in the art will recognize that equivalents of the following supplies and suppliers exist and, as such, the suppliers listed below are not to be construed as limiting.

In general, in addition to the methods described below, the HPCMs of the invention can be made using the exemplary protocols outlined in United States Patent Application No. 2013/0319086 the disclosure of which is incorporated by reference herein.

Characterization

Those skilled in the art will recognize that equivalents of the following instruments and suppliers exist and, as such, the instruments listed below are not to be construed as limiting.

The % C, % H, % N values were measured by combustion analysis (CE-440 Elemental Analyzer; Exeter Analytical Inc., North Chelmsford, MA) or % C by Coulometric Carbon Analyzer (modules CM5300, CM5014, UIC Inc., Joliet, IL). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, GA). The SSA was calculated using the BET method, the SPV was the single point value determined for $P/P_0 > 0.98$ and the APD was calculated from the desorption leg of the isotherm using the BJH method. Scanning electron microscopic (SEM) image analyses were performed (JEOL JSM-5600 instrument, Tokyo, Japan) at 7 kV. Particle sizes were measured using a Beckman Coulter Multisizer 3 analyzer (30 μm aperture, 70,000 counts; Miami, FL). The particle diameter (dp) was measured as the 50% cumulative diameter of the volume based particle size distribution. The width of the distribution was measured as the 90% cumulative volume diameter divided by the 10% cumulative volume diameter (denoted 90/10 ratio). Multinuclear ($^{13}C$, $^{29}Si$) CP-MAS NMR spectra were obtained using a Bruker Instruments Avance-300 spectrometer (7 mm double broadband probe). The spinning speed was typically 5.0-6.5 kHz, recycle delay was 5 sec. and the cross-polarization contact time was 6 msec. Reported $^{13}C$ and $^{29}Si$ CP-MAS NMR spectral shifts were recorded relative to tetramethylsilane using the external standards adamantane ($^{13}C$ CP-MAS NMR, δ 38.55) and hexamethylcyclotrisiloxane ($^{29}Si$ CP-MAS NMR, δ-9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. *Magn. Reson. Chem.* 2002, 40, 70-76] Titrations were performed using a Metrohm 716 DMS Titrino autotitrator with 6.0232.100 pH electrode (Metrohm, Hersau, Switzerland, or equivalent).

Example 1

Synthesis of DEAP HPCM Stationary Phases

DEAP HPCM stationary phases (Phases 1A and 1B) were synthesized according to the following procedure:

Step 1: BEH porous particles (Waters Corporation, Milford, Mass.; 6.5% C; SSA=75-200 $m^2/g$; SPV=0.60-0.75 cc/g; APD=115-310 Å) of the formula $(O_{1.5}SiCH_2CH_2SiO_{1.5})(SiO_2)_4$ (prepared following the method described in U.S. Pat. No. 6,686,035) were refluxed in toluene (5 mL/g, Fisher Scientific, Fairlawn, NJ) using a Dean-Stark trap for 1 hour. Upon cooling, redistilled (N,N-Diethylaminopropyl)trimethoxysilane (DEAP, Silar Laboratories, Wilmington, NC) at 0.3 $\mu mol/m^2$ was added and the reaction was heated to reflux for 2 hrs. The reaction was then cooled and the product was filtered and washed successively with toluene, 1:1 v/v acetone/water, and acetone (all solvents from Fisher Scientific, Fairlawn, NJ). The product was then dried at 80° C. under reduced pressure for 16 hrs.

Step 2: Material from Step 1 was refluxed in toluene (5 mL/g, Fisher Scientific, Fairlawn, NJ) using a Dean-Stark trap for 1 hour. Upon cooling, imidazole (Aldrich, Milwaukee, WI) and octadecyltrichlorosilane (Gelest Inc., Morrisville, PA) at 2.3 $\mu mol/m^2$ were added and the reaction was heated to reflux for 16 hrs. The reaction was then cooled and the product was filtered and washed successively with toluene, 1:1 v/v acetone/water, and acetone (all solvents from Fisher Scientific, Fairlawn, NJ). The material was then refluxed in acetone/aqueous 0.1 M ammonium bicarbonate (pH 10) solution for 20 hours at 50° C. (hydrolysis). Following hydrolysis, the material was washed successively with 1:1 v/v acetone/water, and acetone (all solvents from Fisher Scientific, Fairlawn, NJ). The product was then dried at 80° C. under reduced pressure for 16 hours.

Step 3: Material from Step 2 was refluxed in toluene (5 mL/g, Fisher Scientific, Fairlawn, NJ) using a Dean-Stark trap for 1 hour. Upon cooling, imidazole (Aldrich, Milwaukee, WI) and triethylchlorosilane (TECS, Gelest Inc., Morrisville, PA) were added and the reaction was heated to reflux for 4 hrs. The reaction was then cooled and, imidazole and trimetylchlorosilane (Aldrich, Milwaukee, WI) were added to the reaction and the reaction was heated to reflux for an additional 16 hrs. The reaction was then cooled and the product was filtered and washed successively with toluene, 1:1 v/v acetone/water, and acetone (all solvents from Fisher Scientific, Fairlawn, NJ). The product was then dried at 80° C. under reduced pressure for 16 hrs. Unless otherwise noted, all reagents described in the above procedure (Steps 1 through 3) were used as received. Those skilled in the art will recognize that equivalents exist, as such, although supplies and suppliers are listed, the listed supplies/suppliers should in no way be construed as limiting.

Stationary phases resulting from the above procedure were characterized in the following manner. The % C values were measured by Coulometric Carbon Analyzer (modules CM5300, CM5014, UIC Inc., Joliet, IL). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, GA). The SSA was calculated using the BET method, the SPV was the single point value determined for $P/P_0>0.98$ and the APD was calculated from the desorption leg of the isotherm using the BJH method. Particle sizes were measured using a Beckman Coulter Multisizer 3 analyzer (30 μm aperture, 70,000 counts; Miami, FL). The particle diameter (dp) was measured as the 50% cumulative diameter of the volume based particle size distribution. Total surface coverages of the octadecyltrichlorosilane were determined by the difference in particle % C before and after the surface modification as measured by elemental analysis. Those skilled in the art will recognize that equivalents of the following instruments exist and, as such, the instruments listed below are not to be construed as limiting. Information related to the two DEAP HPCM phases, Phase 1A and Phase 1B, can be found below:

| Base Particle | Material |
|---|---|
| B1 | Hybrid Organic Silica (1.7 μm, 130 Å APD, 185 $m^2/g$ SSA)[1] |
| B2 | Hybrid Organic Silica (1.7 μm, 300 Å APD, 90 $m^2/g$ SSA)[1] |

[1]As described in U.S. Pat. No. 7,919,177, U.S. Pat. No. 7,223,473, U.S. Pat. No. 6,686,035

| Example | Base Material Particle | DEAP Charge ($\mu mol/m^2$) | $C_{18}$ Coverage ($\mu mol/m^2$) |
|---|---|---|---|
| 1A | B1 | 0.3 | 2.4 |
| 1B | B2 | 0.3 | 2.6 |

Example 2

Graphitic and Conventional C18 Reversed Phase Chromatography of Labeled Glycans

N-glycans labeled in accordance with the claimed invention were prepared from Labeling Reagent-1 (RFMS) from human IgG (Sigma 14506) according to previously published conditions. (Lauber, M. A.; Yu, Y. Q.; Brousmiche, D. W.; Hua, Z.; Koza, S. M.; Magnelli, P.; Guthrie, E.; Taron, C. H.; Fountain, K. J., Rapid Preparation of Released N-Glycans for HILIC Analysis Using a Labeling Reagent that Facilitates Sensitive Fluorescence and ESI-MS Detection. Anal Chem 2015, 87 (10), 5401-9.)

Human IgG N-glycans labeled in accordance with the claimed invention were then separated using either graphitic or conventional C18 reversed phased chromatography and a Waters ACQUITY UPLC H-Class Bio LC system. Separations to produce the representative chromatogram shown in FIG. 2 and FIG. 3 were performed using the conditions noted below.

| | |
|---|---|
| Column: | Thermo Scientific Hypercarb Porous Graphitic Carbon LC Column, 250Å, 3 μm, 2.1 × 150 mm Or Waters ACQUITY UPLC BEH C18 130Å, 1.7 μm, 2.1 × 150 mm |
| Mobile Phase A: | 0.1% (v/v) Formic Acid, Water |
| Mobile Phase B: | 0.1% (v/v) Formic Acid, Acetonitrile |
| Column Temperature: | 60° C. |
| Injection Volume: | 4 μL |
| Sample Concentration: | 10 pmol/μL |
| Sample Diluent: | Water |
| Fluorescence Detection: | Ex 265 nm/Em 425 nm (10 Hz) |

| Gradient Table: | | | | | |
|---|---|---|---|---|---|
| Time (min) | Flow | Rate (mL/min) | % A | % B | Curve |
| Initial | 0.200 | 99.5 | 0.5 | Initial | |
| 60.00 | 0.200 | 10.0 | 90.0 | 6 | |
| 61.00 | 0.200 | 10.0 | 90.0 | 6 | |

| | | | | | |
|---|---|---|---|---|---|
| 62.00 | 0.200 | 99.5 | 0.5 | 6 | |
| 75.00 | 0.200 | 99.5 | 0.5 | 6 | |

MS Conditions

| | |
|---|---|
| Polarity | ES+ |
| Acquistions: | 700-2000 m/z (1 Hz) |
| Capillary (kV) | 3 |
| Source Temperature (° C.) | 100 |
| Sampling Cone | 30 |
| Source Offset | 50 |
| Desolvation Temperature (° C.) | 300 |
| Desolvation Gas Flow (L/Hr) | 800 |
| Nebuliser Gas Flow (Bar) | 7.0 |

Example 3

Separation of Labeled Glycans Using HPCM and Formic Acid Mobile Phases

Labeled human IgG N-glycans were separated using a Waters ACQUITY UPLC CSH C18 column and a Waters ACQUITY UPLC H-Class Bio LC system. Separations to produce the representative chromatograms shown in FIG. 4 were performed using the conditions noted below.

LC Conditions

| | |
|---|---|
| Column: | Waters ACQUITY UPLC CSH C18 130Å, 1.7 µm, 2.1 × 150 mm |
| Mobile Phase A: | 0.1% (v/v) Formic Acid, Water |
| Mobile Phase B: | 0.1% (v/v) Formic Acid, Acetonitrile |
| Column Temperature: | 60° C. |
| Injection Volume: | 4 µL |
| Sample Concentration: | 10 pmol/µL |
| Sample Diluent: | Water |
| Fluorescence Detection: | Ex 265 nm/Em 425 nm (10 Hz) |

Gradient Table:

| Time (min) | Flow Rate (mL/min) | % A | % B | Curve |
|---|---|---|---|---|
| Initial | 0.200 | 99.5 | 0.5 | Initial |
| 60.00 | 0.200 | 10.0 | 90.0 | 6 |
| 61.00 | 0.200 | 10.0 | 90.0 | 6 |
| 62.00 | 0.200 | 99.5 | 0.5 | 6 |
| 75.00 | 0.200 | 99.5 | 0.5 | 6 |

Example 4

LC-Fluorescence-MS Analysis of Labeled Glycans Using HPCM and Various Aqueous Mobile Phase Additives Labeled human IgG N-glycans were analyzed using a Waters ACQUITY UPLC CSH C18 column, a Waters ACQUITY UPLC H-Class Bio LC system, and a Waters Synapt G2-S mass spectrometer. Method selectivity and sensitivity were modulated through the use of various aqueous mobile phase additives, including formic acid, acetic acid, ammonium formate, and/or ammonium acetate (FIG. 5). Details of how these separations were performed can be found below.

LC Conditions

| | |
|---|---|
| Column: | Waters ACQUITY UPLC CSH C18 130Å 1.7 µm 2.1 × 150 mm |
| Mobile Phase A (1): | 0.1% (v/v) Formic Acid, Water |
| Mobile Phase A (2): | 50 mM Ammonium Formate/ 10 mM Formic Acid |
| Mobile Phase A (3): | 5 mM Ammonium Formate/ 5 mM Formic Acid |
| Mobile Phase A (4): | 1 mM Ammonium Formate/ 1 mM Formic Acid |
| Mobile Phase A (5): | 17 mM Acetic Acid/ 1 mM Ammonium Acetate |
| Mobile Phase A (6): | 17 mM Acetic Acid/ 1 mM Ammonium Formate |
| Mobile Phase B: | Acetonitrile |
| Column Temperature: | 60° C. |
| Injection Volume: | 4 µL |
| Sample Concentration: | 10 pmol/µL |
| Sample Diluent: | Water |
| Fluorescence Detection: | Ex 265 nm/Em 425 nm (10 Hz) |

Gradient Table:

| Time(min) | Flow Rate (mL/min) | % A | % B | Curve |
|---|---|---|---|---|
| Initial | 0.200 | 99.5 | 0.5 | Initial |
| 21.50 | 0.200 | 68.0 | 32.0 | 6 |
| 22.50 | 0.200 | 10.0 | 90.0 | 6 |
| 23.50 | 0.200 | 99.5 | 0.5 | 6 |
| 39.00 | 0.200 | 99.5 | 0.5 | 6 |

MS Conditions

| | |
|---|---|
| Polarity | ES+ |
| Acquisition: | 700-2000 m/z |
| Capillary (kV) | 3 |
| Source Temperature (° C.) | 100 |
| Sampling Cone | 30 |
| Source Offset | 50 |
| Desolvation Temperature (° C.) | 300 |
| Desolvation Gas Flow (L/Hr) | 800 |
| Nebuliser Gas Flow (Bar) | 7.0 |

Labeling Reagent-1 (RFMS)

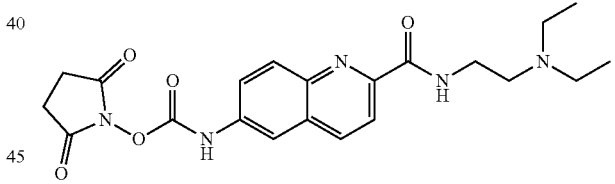

Example 5

Constant Ionic Strength for Separations of Highly Sialylated Labeled Glycans Using HPCM Labeled N-glycans were prepared from bovine fetuin (Sigma F3004) according to a previously published protocol (Lauber, M. A.; Yu, Y. Q.; Brousmiche, D. W.; Hua, Z.; Koza, S. M.; Magnelli, P.; Guthrie, E.; Taron, C. H.; Fountain, K. J., Rapid Preparation of Released N-Glycans for HILIC Analysis Using a Labeling Reagent that Facilitates Sensitive Fluorescence and ESI-MS Detection. Anal Chem 2015, 87 (10), 5401-9) and subsequently analyzed by LC-Fluorescence-MS using an ACQUITY UPLC CSH C18 column, a Waters ACQUITY UPLC H-Class Bio LC system, and a Waters Synapt G2-S mass spectrometer. The representative chromatograms displayed in FIG. 6 were obtained using the following method conditions:

LC Conditions

| | |
|---|---|
| Column: | Waters ACQUITY UPLC CSH C18 130Å 1.7 μm 2.1 × 150 mm |
| Mobile Phase A (6): | 17 mM Acetic Acid/1 mM Ammonium Formate |
| Mobile Phase B (1): | 40:60 Water/Acetonitrile |
| Mobile Phase B (2): | 17 mM Acetic Acid/1 mM Ammonium Formate in 40:60 Water/Acetonitrile |
| Mobile Phase B (3): | 34 mM Acetic Acid/2 mM Ammonium Formate in 40:60 Water/Acetonitrile |
| Mobile Phase B (4): | 85 mM Acetic Acid/5 mM Ammonium Formate in 40:60 Water/Acetonitrile |
| Column Temperature: | 60° C. |
| Injection Volume: | 3 μL |
| Sample Concentration: | Glycans from 0.17 μg of fetuin per μL |
| Sample Diluent: | 200 mM Ammonium Acetate in 5% Acetonitrile |
| Fluorescence Detection: | Ex 265 nm/Em 425 nm (10 Hz) |

Gradient Table:

| Time(min) | Flow Rate (mL/min) | % A | % B | Curve |
|---|---|---|---|---|
| Initial | 0.200 | 99.2 | 0.8 | Initial |
| 21.50 | 0.200 | 46.7 | 53.3 | 6 |
| 22.50 | 0.200 | 0.0 | 100.0 | 6 |
| 23.50 | 0.200 | 99.2 | 0.8 | 6 |
| 39.00 | 0.200 | 99.2 | 0.8 | 6 |

MS Conditions

| | |
|---|---|
| Polarity | ES+ |
| Acquisition: | 700-2000 m/z |
| Capillary (kV) | 3 |
| Source Temperature (° C.) | 100 |
| Sampling Cone | 30 |
| Source Offset | 50 |
| Desolvation Temperature (° C.) | 300 |
| Desolvation Gas Flow (L/Hr) | 800 |
| Nebuliser Gas Flow (Bar) | 7.0 |

Example 6

Exemplary Embodiments of Using HPCM to Separate Labeled Glycans

Labeled human IgG and bovine fetuin N-glycans were analyzed by LC-Fluorescence-MS using an ACQUITY UPLC CSH C18 column, a Waters ACQUITY UPLC H-Class Bio LC system, and a Waters Synapt G2-S mass spectrometer. The representative chromatograms displayed in FIG.

LC Conditions

| | |
|---|---|
| Column: | Waters ACQUITY UPLC CSH C18 130Å 1.7 μm 2.1 × 150 mm |
| Mobile Phase A: | 17 mM Acetic Acid/ 1 mM Ammonium Formate |
| Mobile Phase B: | 17 mM Acetic Acid/ 1 mM Ammonium Formate in 40:60 Water/Acetonitrile |
| Column Temperature: | 60° C. |
| Injection Volume: | 3 μL (fetuin glycans), 4 μL (human IgG glycans) |
| Sample Concentration: | Glycans from 0.17 μg of fetuin per μL (fetuin glycans), 10 pmole/μL (human IgG glycans) |
| Sample Diluent: | 200 mM Ammonium Acetate in 5% Acetonitrile (fetuin glycans), water (human IgG glycans) |
| Fluorescence Detection: | Ex 265 nm/Em 425 nm (10 Hz) |

Gradient Table:

| Time(min) | Flow Rate(mL/min) | % A | % B | Curve |
|---|---|---|---|---|
| Initial | 0.400 | 100.0 | 0.00 | Initial |
| 49.00 | 0.400 | 70.0 | 30.0 | 6 |
| 49.30 | 0.400 | 0.0 | 100.0 | 6 |
| 49.60 | 0.400 | 0.0 | 100.0 | 6 |
| 49.90 | 0.400 | 100.0 | 0.0 | 6 |
| 58.00 | 0.400 | 100.0 | 0.0 | 6 |

MS Conditions

| | |
|---|---|
| Polarity | ES+ |
| Acquisition: | 700-2000 m/z (1 Hz) |
| Capillary (kV) | 3 |
| Source Temperature (° C.) | 100 |
| Sampling Cone | 30 |
| Source Offset | 50 |
| Desolvation Temperature (° C.) | 300 |
| Desolvation Gas Flow (L/Hr) | 800 |
| Nebuliser Gas Flow (Bar) | 7.0 |

Example 7

Optimization of Method Conditions for Separations of Labeled Human IgG Glycans with DEAP HPCM Labeled human IgG N-glycans were analyzed using a DEAP HPCM column and a Waters ACQUITY UPLC H-Class Bio LC system. Method selectivity was modulated through the use of various aqueous mobile phase additives, including formic acid, acetic acid, ammonium formate, and/or ammonium acetate (FIG. 8). Details of how these separations were performed can be found below.

LC Conditions

| | |
|---|---|
| Column: | Waters DEAP HPCM 130Å 1.7 μm (Phase 1A) 2.1 × 150 mm |
| Mobile Phase A (1): | 17 mM Acetic Acid/ 1 mM Ammonium Formate |
| Mobile Phase A (2): | 1 mM Formic Acid/ 1 mM Ammonium Formate |
| Mobile Phase B (1): | 20:80 Water/Acetonitrile |
| Mobile Phase B (2): | 10 mM Formic Acid/10 mM Ammonium Formate in 20:80 Water/Acetonitrile |
| Column Temperature: | 60° C. |
| Injection Volume: | 4 μL |
| Sample Concentration: | 10 pmol/μL |
| Sample Diluent: | Water |
| Fluorescence Detection: | Ex 265 nm/Em 425 nm (10 Hz) |

Gradient Table:

| Time (min) | Flow Rate (mL/min) | % A | % B | Curve |
|---|---|---|---|---|
| Initial | 0.200 | 99.4 | 0.6 | Initial |
| 21.50 | 0.200 | 60.0 | 40.0 | 6 |
| 22.50 | 0.200 | 10.0 | 90.0 | 6 |
| 23.50 | 0.200 | 99.4 | 0.6 | 6 |
| 39.00 | 0.200 | 99.4 | 0.6 | 6 |

Example 8

Optimization of Method Conditions for Separations of Labeled Fetuin Glycans with DEAP HPCM Labeled fetuin N-glycans were analyzed using a DEAP HPCM column and a Waters ACQUITY UPLC H-Class Bio LC system. Method selectivity was modulated through the use of various aqueous mobile phase additives, including formic acid, acetic acid, ammonium formate, and/or ammonium acetate (FIG. 9). Details of how these separations were performed can be found below.

LC Conditions

| | |
|---|---|
| Column: | Waters DEAP HPCM 130Å 1.7 μm (Phase 1A) 2.1 × 150 mm |
| Mobile Phase A: | 99.5:0.5 Water/Acetonitrile |
| Mobile Phase B (1): | 18.9 mM Formic Acid/18.9 mM Ammonium Formate in 40:60 Water/Acetonitrile |
| Mobile Phase B (2): | 37.8 mM Formic Acid/37.8 mM Ammonium Formate in 40:60 Water/Acetonitrile |
| Mobile Phase B (3): | 94.5 mM Formic Acid/94.5 mM Ammonium Water/Acetonitrile Formate in 40:60 |
| Column Temperature: | 60° C. |
| Injection Volume: | 3 μL |
| Sample Concentration: | Glycans from 0.17 μg of fetuin per μL |
| Sample Diluent: | 200 mM Ammonium Acetate in 5% Acetonitrile |
| Fluorescence Detection: | Ex 265 nm/Em 425 nm (10 Hz) |

Gradient Table:

| Time (min) | Flow Rate (mL/min) | % A | % B | Curve |
|---|---|---|---|---|
| Initial | 0.200 | 100.0 | 0.0 | Initial |
| 21.50 | 0.200 | 47.1 | 52.9 | 6 |
| 22.50 | 0.200 | 0.0 | 100.0 | 6 |
| 23.50 | 0.200 | 100.0 | 0.0 | 6 |
| 39.00 | 0.200 | 100.0 | 0.0 | 6 |

Example 9

Exemplary Embodiments of Using DEAP HPCM to Separate Labeled Glycans Labeled human IgG and bovine fetuin N-glycans were analyzed by LC-Fluorescence-MS using a DEAP HPCM column, a Waters ACQUITY UPLC H-Class Bio LC system, and a Waters Synapt G2-S mass spectrometer. The representative chromatograms and representative mass spectrum displayed in FIG. 10 and FIG. 12 were obtained using the following method conditions:

LC Conditions

| | |
|---|---|
| Column: | DEAP HPCM 130Å 1.7 μm (Phase 1A) 2.1 × 150 mm |
| Mobile Phase A: | Water |
| Mobile Phase B: | 100 mM Formic Acid/100 mM Ammonium Formate in 40:60 Water/Acetonitrile |
| Column Temperature: | 60° C. |
| Injection Volume: | 3 μL (fetuin glycans), 4 μL (human IgG glycans) |
| Sample Concentration: | Glycans from 0.17 μg of fetuin per μL (fetuin glycans), 10 pmole/μL (human IgG glycans) |
| Sample Diluent: | 200 mM Ammonium Acetate in 5% Acetonitrile (fetuin glycans), water (human IgG glycans) |
| Fluorescence Detection: | Ex 265 nm/Em 425 nm (10 Hz) |

Gradient Table:

| Time(min) | Flow | Rate (mL/min) | % A | % B | Curve |
|---|---|---|---|---|---|
| Initial | 0.400 | 100.0 | 0.00 | Initial | |
| 36.00 | 0.400 | 78.0 | 22.0 | 6 | |
| 36.30 | 0.400 | 0.0 | 100.0 | 6 | |
| 36.60 | 0.400 | 0.0 | 100.0 | 6 | |
| 36.90 | 0.400 | 100.0 | 0.0 | 6 | |
| 45.00 | 0.400 | 100.0 | 0.0 | 6 | |

Example 10

Increasing Ionic Strength During the Initial Conditions of a Method to Improve Separations of Labeled Glycans Two exemplary separations have been obtained using the DEAP stationary phase (FIG. 10), as described below. FIG. 10A presents a chromatogram for labeled hIgG N-glycans in which superior resolution is achieved among the mono- and di-sialylated structures (S1 and S2 structures). Neutral structures, on the other hand, are separated with slightly inferior resolution compared to other materials (refer to FIG. 7A), though implementing higher ionic strengths during the initial condition of the gradient can increase resolution on the DEAP stationary phase, especially with respect to afucosylated and bisecting GlcNAc (N-acetylglucosamine) structures (FIG. 11). While not limited to theory, it is believed that some ionic strength in the initial step of the separation favorably reduces the ionic repulsion between the base particle of the charged surface reverse phase material and the neutral glycans that upon labeling bear an amphipathic, strongly basic moiety. FIG. 10B presents an exemplary result for the use of DEAP to analyze highly sialylated, high antennarity labeled glycans from bovine fetuin. With this charged surface reversed phase material and the developed technique, an extraordinary degree of resolution is achieved, most notably for the trisialylated, triantennary structures (S3) that dominate the chromatogram. A striking capability of this methodology is the ability to resolve fine structure at the front of the retention window corresponding to the trisialylated (S3) structures. By MS analysis, this chromatographic fine structure has been confirmed to correspond to +16 Da forms of the S3 species, which can usually be attributed to the presence of a form of a non-human sialic acid known as N-glycolyl neuraminic acid, NGNA (versus N-acetyl neuraminic acid, NANA) (FIG. 10B inset). This is a highly significant capability of this invention, as sialylated glycans containing N-glycolyl neuraminic acid can potentially cause immunogenic responses in patients if they are present on biopharmaceuticals. Sialylated glycans containing N-glycolyl neuraminic acid have also been found to be a biomarker associated with long-term red meat consumption,[9] and their presence has been implicated as a cancer risk factor. Given the unique selectivity associated with the use of charged surface reversed phase materials, it is not unreasonable to assert that this technology could be further optimized to enable even higher resolution of N-glycolyl neuraminic acid containing glycan species. Undoubtedly, it is valuable to have sensitive techniques for monitoring these species even when they are present in samples at low relative abundances.

One advantage to the use of the DEAP HPCM charged surface reversed material is that the optimal chromatographic conditions for glycans labeled with amphipathic, strongly basic residues happen to also be suitable conditions for their analysis by ESI+MS. Labeled glycans from bovine fetuin can, for instance, be analyzed with the DEAP HPCM stationary phase such that comparable signal-to-noise is achieved for both fluorescence and MS detection (FIG. 12). It is also noteworthy that the peak profiles among the two chromatograms are in good agreement. Furthermore, the mass spectra that can be extracted from these analyses are indeed exemplary in exhibiting high signal-to-noise (FIG. 12B).

Labeled human IgG N-glycans were separated with methods varying with respect to ionic strength during the initial conditions of a gradient. Samples were analyzed by LC-Fluorescence using a DEAP HPCM column and a Waters ACQUITY UPLC H-Class Bio LC system. The chromatograms displayed in FIG. 11 were obtained using the following method conditions:

LC Conditions

| Column: | Waters DEAP HPCM 130Å 1.7 μm (Phase 1A) 2.1 × 150 mm |
|---|---|
| Mobile Phase A: | Water |
| Mobile Phase A (1): | 2.5 mM NH4 Formate/2.5 mM Formic Acid |
| Mobile Phase A (2): | 5 mM NH4 Formate/5 mM Formic Acid |
| Mobile Phase B (3): | 100 mM Formic Acid/100 mM Ammonium Formate in 40:60 Water/Acetonitrile |
| Column Temperature: | 60° C. |
| Injection Volume: | 4 μL |
| Sample Concentration: | 10 pmole/μL |
| Sample Diluent: | Water |
| Fluorescence Detection: | Ex 265 nm/Em 425 nm (10 Hz) |

Gradient Table:

| Time(min) | Flow Rate(mL/min) | % A | % B | Curve |
|---|---|---|---|---|
| Initial | 0.400 | 100.0 | 0.00 | Initial |
| 36.00 | 0.400 | 78.0 | 22.0 | 6 |
| 36.30 | 0.400 | 0.0 | 100.0 | 6 |
| 36.60 | 0.400 | 0.0 | 100.0 | 6 |
| 36.90 | 0.400 | 100.0 | 0.0 | 6 |

Example 11

Optimized Separations of Released Fetuin Glycans Labeled with Various Amphipathic, Strongly Basic Moieties Procaine and procainamide labeled N-glycans were prepared from bovine fetuin (Sigma F3004) according to a previously published protocol (Lauber, M. A.; Yu, Y. Q.; Brousmiche, D. W.; Hua, Z.; Koza, S. M.; Magnelli, P.; Guthrie, E.; Taron, C. H.; Fountain, K. J., Rapid Preparation of Released N-Glycans for HILIC Analysis Using a Labeling Reagent that Facilitates Sensitive Fluorescence and ESI-MS Detection. Anal Chem 2015, 87 (10), 5401-9.) and subsequently analyzed by LC-Fluorescence-MS using a DEAP HPCM 130 Å 1.7 μm (Phase 1A) column, and a Waters ACQUITY UPLC H-Class Bio LC system. The representative chromatograms displayed in FIG. 13 were obtained using the method conditions listed in Example 9. Fluorescence detector wavelengths for the procaine (labeling reagent-2) labeled glycans were Ex 295/Em 335 nm and Ex 265/Em 345 nm for the procainamide (labeling reagent-3) labeled glycans.

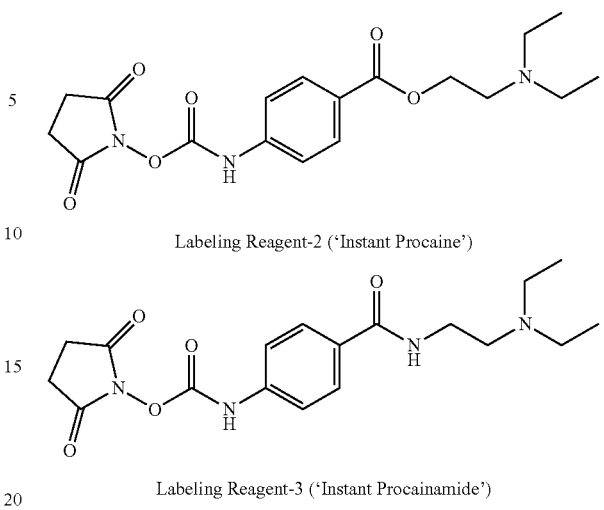

Labeling Reagent-2 ('Instant Procaine')

Labeling Reagent-3 ('Instant Procainamide')

Example 12

Comparison Example Corresponding to Separations of Labeled Human IgG and Fetuin N-Glycans Using a DEAP HPCM Versus a GlycanPac AXR-1 Column The methods and materials described as part of this invention are distinct from the anion exchange mixed mode materials and glycan analysis methods previously described by Liu, Aich, and Pohl in US patent application publication number US20140178912. In their exemplary embodiment of an anion exchange, reverse phase material, Liu, Auch and Pohl defined a stationary phase (Phase 21) that was created via bonding with one ligand comprised of a neutral, ten carbon alkyl chain terminated in a hydrophilic amide group and a second ligand consisting of an eleven carbon alkyl chain terminated in a dimethylated, tertiary amine.

It is believed that Phase 21 has been made commercially available by Thermo Scientific in the form of the GlycanPac AXR-1 columns (i.e. Thermo Scientific Catalog 088136). Herein, chromatographic separations achieved with DEAP HPCM are contrasted with those obtained with GlycanPac AXR-1. FIG. 14 shows separations of labeled hIgG glycans using the charged surface reverse phase material (DEAP HPCM, Phase 1A) with its optimal use conditions versus a commercially available mixed mode GlycanPac AXR-1 column with identical use conditions and others tailored to improve performance for these types of glycans.

MS detection of labeled glycans that compares well with the established technique of fluorescence detection is enabling in that the similar chromatographic profiles are obtained with either detection mode. At this time, MS detectors are still not routinely employed in QC laboratories. The strongly basic moiety and the quinoline ring structure of the Labeled labeling reagent are the key to providing similar signal to noise ratios in both MS and fluorescence modes. This reagent characteristic enables the immediate interrogation of unknown peaks that might be observed during QC testing. The same sample can be examined by MS in a support facility running under the exact conditions used in a QC laboratory. The concomitant use of this label and the charged surface materials described in this disclosure enables a straight forward sample interrogation, which might otherwise require re-labeling the sample with an MS compatible reagent, development of an LC method, and identification of the unknown peak. Glycans labeled with a strongly basic moiety are challenging to optimally separate with the GlycanPac AXR-1 column. The placement of the ionizable modifier group (the tertiary amine in this case) at the end of the ligands on Phase 21 (and presumably the GlycanPac AXR-1 phase, see FIG. 16) accentuates the ion-exchange character of the column, which is to the detriment of separating glycans with a positively charged label. The ionic strength of the mobile phase can be increased to mitigate ionic repulsion and increase retention, but this can also mitigate the ionic attraction that is desirable in the class separation of sialylated glycans. The charged surface reversed phase materials are optimized to provide good peak shape (enabling high resolution), and retention (necessary for the selective separation of charged analytes) under low ionic strength conditions (required for sensitive MS analyses).[10-13] FIG. 14 clearly illustrates the impact of the placement on the charged group at the surface compared to the end of the ligand. Notice that while labeled hIgG glycans are strongly retained and well resolved with the DEAP HPCM (Phase 1A) material, they elute in the void when injected onto and separated under the same conditions on a GlycanPac AXR-1 column. Quite clearly, these glycans labeled with amphipathic, strongly basic moieties are very strongly repelled by the GlycanPac AXR-1 stationary phase, to an extent that is remarkably different in magnitude than both the commercially available HPCM stationary phase and the DEAP HPCM stationary phase. In addition, it is found that the glycans of importance to this invention can only be retained on a GlycanPac AXR-1 column when high ionic strength conditions are used during the initial step of the separation; and even then, retention and resolution remain inadequate for an analysis. Notably, labeled tri- and tetra-sialylated glycans are better retained on the GlycanPac AXR-1 stationary phase. Yet, even when used with optimized conditions, the GlycanPac AXR-1 stationary phase yields separation resolution that is observed to be inferior to that of the like particle size, DEAP HPCM (Phase 1A) (FIG. 15). It is believed that the inferior performance of the GlycanPac AXR-1 material is due to the positioning and accessibility of its ionizable modifier (FIG. 16). On Phase 21 of US patent application publication number US20140178912, the tertiary amine, ionizable modifier is at the terminal end of a ligand that is equivalent in length to the other, more abundant neutral group, which itself is comprised of an alkyl chain and an amide terminal group. Accordingly, the interface of the bonded phase and mobile phase will itself have a positive potential. In addition, the interface will be dominated with polar amide terminal groups. It is these attributes of Phase 21 that are believed to be responsible for its poor applicability to glycans that are modified with amphipathic, strongly basic residues.

Conditions

The conditions provided in Example 9 were used here to produce an exemplary separation of labeled human IgG and fetuin N-glycans using the DEAP HPCM stationary phase. The same method conditions were also used, as shown in FIG. 14 and FIG. 15, for separations using a Thermo Scientific GlycanPac AXR-1 column. In addition, the following conditions were employed in an attempt to optimize the use of a GlycanPac AXR-1 column for separations of labeled human IgG N-glycans:

| LC Conditions | |
|---|---|
| Column: | Thermo Scientific GlycanPac AXR-1 2.1 × 150 mm |
| Mobile Phase A: | 10 mM Ammonium Formate/ 10 mM Formic Acid |
| Mobile Phase B: | 200 mM Formic Acid/ 200 mM Ammonium Formate in 40:60 Water/Acetonitrile |
| Column Temperature: | 60° C. |
| Injection Volume: | 3 µL (fetuin glycans), 4 µL (human IgG glycans) |
| Sample Concentration: | Glycans from 0.17 µg of fetuin per µL(fetuin glycans), 10 pmole/µL (human IgG glycans) |
| Sample Diluent: | 200 mM Ammonium Acetate in 5% Acetonitrile (fetuin glycans), water (human IgG glycans) |
| Fluorescence Detection: | Ex 265 nm/ Em 425 nm (10 Hz) |

| Gradient Table: | | | | | |
|---|---|---|---|---|---|
| Time(min) | Flow | Rate (mL/min) | % A | % B | Curve |
| Initial | 0.400 | 100.0 | 0.00 | Initial | |
| 36.00 | 0.400 | 78.0 | 22.0 | 6 | |
| 36.30 | 0.400 | 0.0 | 100.0 | 6 | |
| 36.60 | 0.400 | 0.0 | 100.0 | 6 | |
| 36.90 | 0.400 | 100.0 | 0.0 | 6 | |

INCORPORATION BY REFERENCE

The entire contents of all patents published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for selectively isolating glycans from a sample based on the net charge of each glycan, the method comprising:
   a) reacting a sample comprising glycans with a labeling reagent to produce labeled glycans;
   b) loading the labeled glycans onto a chromatographic separation device comprising a high purity chromatographic material comprising a chromatographic surface wherein the chromatographic surface is charged and comprises a hydrophobic surface group and one or more ionizable modifiers, such that the labeled glycans are selectively adsorbed onto the high purity chromatographic material;
   c) selectively eluting the adsorbed labeled glycans from the high purity chromatographic material, the selective elution including:
   exposing the labeled adsorbed glycans on the high purity chromatographic material to an aqueous mobile phase, the aqueous mobile phase comprising a concentration of a buffer and a concentration of an organic solvent, increasing the concentration each of the buffer and the organic solvent, thereby varying ionic strength of the aqueous mobile phase, and selectively separating the labeled glycans from the high purity chromatographic material based on the net charge of each glycan and the ionic strength of the aqueous mobile phase;

wherein the organic solvent comprises water and acetonitrile and the buffer is selected from the group consisting of a first buffer comprising ammonium formate and formic acid, a second buffer comprising ammonium formate and acetic acid, and a third buffer comprising ammonium acetate and acetic acid.

2. The method of claim 1, wherein the glycans are N-glycans.

3. The method of claim 1, wherein the glycans are hIgG glycans, Fetuin glycans, FA2BG2S2, FA2G2S1, or FA2G2.

4. The method of claim 1, wherein the labeling reagent is an MS active, rapid fluorescence tagging compound, a procainamide reagent, or a procaine reagent.

5. The method of claim 1, wherein the labeling reagent provides an amphipathic, strongly basic moiety having a Log P value between 0 and 5.

6. The method of claim 1, wherein the labeling reagent provides an amphipathic, strongly basic moiety having a pKa value greater than 6.

7. The method of claim 1, wherein the labeling reagent is a reagent having the formula:

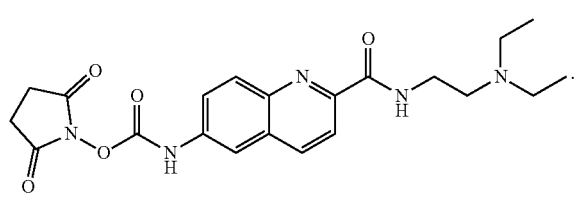 [SMILES: CCN(CC)CCNC(=O)c1ccc2cc(NC(=O)ON3C(=O)CCC3=O)ccc2n1]

8. The method of claim 1, wherein the high purity chromatographic material further comprises a chromatographic core material.

9. The method of claim 1, wherein one of the one or more ionizable modifiers on the chromatographic surface is provided by reacting the chromatographic surface with an ionizable modifying reagent selected from groups having the formula (I)

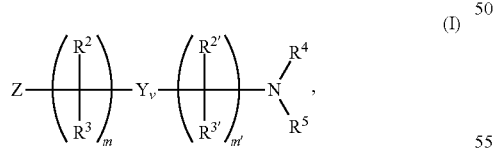

the formula (II):

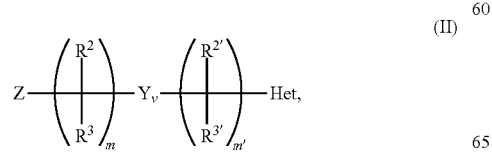

the formula (III):

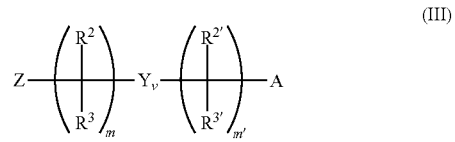

or a combination thereof
wherein
m is an integer from 1-8;
v is 0 or 1;
when v is 0, m' is 0;
when v is 1, m' is an integer from 1-8;
Z represents a chemically reactive group, selected from

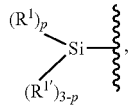

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

Y is an embedded polar functionality;

each occurrence of R$^1$ independently represents a chemically reactive group on silicon, selected from —H, —OH, —OR$^6$, dialkylamine, triflate, Br, Cl, I, vinyl, alkene, or —(CH$_2$)$_{m''}$Q;

each occurrence of Q is —OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

m" is an integer from 1-8 p is an integer from 1-3;

each occurrence of R$^{1'}$ independently represents F, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, fluoroalkyl, or fluoroaryl;

each occurrence of R$^2$, R$^{2'}$, R$^3$ and R$^{3'}$ independently represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_2$-C$_{18}$ heterocycloalkyl, C$_5$-C$_{18}$ aryl, C$_5$-C$_{18}$ aryloxy, or C$_4$-C$_{18}$ heteroaryl, —Z, or a group having the formula —Si(R')$_b$R"$_a$ or —C(R')$_b$R"$_a$;

a and b each represents an integer from 0 to 3 provided that a+b=3;

R' represents a C$_1$-C$_6$ straight, cyclic or branched alkyl group;

R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety;

R$^4$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;

R$^5$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;

each occurrence of $R^6$ independently represents $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

Het represents a heterocyclic or heteroaryl ring system comprising at least one nitrogen atom; and A represents an acidic ionizable modifier moiety or a dual charge ionizable modifier moiety.

10. The method of claim 1, wherein the hydrophobic surface group is a C4 to C30 bonded phase, an aromatic, a phenylalkyl, a fluoro-aromatic, a phenylhexyl, a pentafluorophenylalkyl, or a chiral bonded phase.

11. The method of claim 8, wherein the chromatographic core material comprises a silica material or a hybrid inorganic/organic material.

12. The method of claim 1, wherein the high purity chromatographic material is a stationary phase prepared with a diethylaminoethyl, dimethylaminoethyl, dimethylaminopropyl, dimethylaminoethyl, or diethylaminopropyl (DEAP) modifier.

13. The method of claim 1, wherein the buffer solution has a pH range of 1 to 8.

14. The method of claim 1, wherein the chromatographic separations device is a device selected from the group consisting of a chromatographic column, a thin layer plate, a filtration membrane, a microfluidic separation device, a sample cleanup device, a solid support, a solid phase extraction device, a microchip separation device, and a microtiter plate.

15. The method of claim 1, further comprising treating the separated, labeled glycans with a secondary chromatographic separations device to further isolate, purify, or separate the glycans.

16. The method of claim 1, wherein one of the one or more ionizable modifiers contains an amino group.

17. The method of claim 1, wherein increasing the concentration of each of the buffer and the organic solvent further varies the pH of the aqueous mobile phase.

18. The method of claim 1, wherein the glycans have varying degrees of sialyation, and the selectively separating of the labeled glycans from the high purity chromatographic material is further based on the degree of sialyation of each glycan.

19. The method of claim 12, wherein the high purity chromatographic material is a stationary phase prepared with a diethylaminopropyl (DEAP) modifier.

20. The method of claim 2, wherein the N-glycans comprise acidic residues.

21. The method of claim 18, wherein the glycans are neutral, monosialylated, di-sialylated, tri-sialylated, or a combination thereof.

22. The method of claim 21, wherein the c) selective eluting of the labeled glycans from the high purity chromatographic material further selectively isolates glycans from the sample based on the degree of sialyation of each glycan.

* * * * *